United States Patent [19]
Gorman

[11] Patent Number: 5,932,241
[45] Date of Patent: *Aug. 3, 1999

[54] CATIONIC LIPID DNA COMPLEXES FOR GENE TARGETING

[75] Inventor: Cori M. Gorman, San Francisco, Calif.

[73] Assignee: Valentis, Incorporated, Burlingame, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/480,923

[22] Filed: Jun. 7, 1995

[51] Int. Cl.$^6$ .............................. A61K 9/127; C12N 5/00; C12N 15/00

[52] U.S. Cl. ...................... 424/450; 435/320.1; 435/455; 435/458

[58] Field of Search .......................... 514/44; 435/172.3, 435/320.1, 366, 371, 364, 455, 458; 424/450

[56] References Cited

PUBLICATIONS

Felgner et al (1987) Proced. Natl. Acad. Sci. 84, 7413–7417.
Crystal et al (1994) Nature Genetics 8, 42–51.
Korst et al (1995) Am. J. Respir. Crit. Care Med. 151, 575–587.
Bertling, "Transfection of a DNA/Protein Complex into Nuclei of Mamalian Cells Using Polyoma Capsids and Electroporation," *Bioscience Reports*, 7: 107–112 (1987).
Rahman et al., *Life Sci.*, 31; 2061–2071 (1982).
Smithies et al., "Insertion of DNA Sequences into the Human Chromosomal β–globin locus by homologous recombination," *Nature*, 317: 230–234 (1985).
Thomas & Capecchi, "Site–Directe Mutagenesis by Gene Targeting in Mouse Embryo–Derived Stem Cells," *Cell*, 51: 503–512 (1987).
Yoshimura et al., "Expression of the Human Cystic Fibrosis Transmembrane Conductance Regulator Gene in the Mouse Lung," *Nucleic Acids Research*, 20: 3233–3240 (1992).
Yoshimura et al. (1992) "Expression of the Human Cystic Fibrosis Transmembrane Conductance Regulator Gene in the Mouse Lung after in vivo Intratrachael Plasmid–Mediated Gene Transfer" *Nucleic Acids Research*, 20:32233–3240.
Wu and Wu (1988) "Receptor–Mediated Gene Delivery and Expression In Vivo" *J. Biol. Chem.*, 263:14621–14624.
Wolff et al. (1990) "Direct Gene Transfer into Mouse Muscle in vivo" *Science*, 247:1465–1468.
Wang and Huang (1987) "pH.Sensitive Immunoliposomes Mediate Target–Cell–Specific Delivery and Controlled Expression of a Foreign Gene in Mouse" *Proc. Natl. Acad. Sci. (USA)*, 84:7851–7855.

Nabel et al. (1990) "Site–Specific Gene Expression in vivo by Direct Gene Transfer into the Arterial Wall" *Science*, 249:1285–1288.
Hazinski et al. (1991) "Localization and Induced Expression of Fusion Genes in the Rat Lung" *Am. J. Resp. Cell Molec. Biol.*, 4:206–209.
Stribling et al. (1992) "Aerosol Gene Delivery in vivo" *Proc. Natl. Aad. Sci. (USA)* 89:11277–11281.
Malone et al. (1989) "Cationic Liposome–Mediated RNA Transfection" *Proc. Natl. Acad. Sci (USA)*, 86:6077–6081.
Felgner et al. (1987) "Lipofection: A Highly Efficient, Lipid–Mediated DNA–Transfection Procedure" *Proc. Natl. acad. Sci. (USA)*, 84:7413–7416.
Debs et al. (1990) "Regulation of Gene Expression in vivo by Liposome–Mediated Delivery of a Purified Transcription Factor" *J. Biol. Chem.*,265:10189–10192.
Canonico et al. (1991) "Expression of a CMV Promoter Driven Human alpha–1 Antitrypsin Gene . . . " *Clincal Research*, 39:216A.
Straubinger and Papahadjopoulos (1983) "Liposomes as Carriers for Intracellular Delivery of Nucleic Acids" *Methods of Enzymology*, 101:512–527.
Olson et al. (1979) "Preparation of Liposomes of Defined Size Distribution by Extrusion Through Polycaronate Membranes" *Biochem. Biophys. Acta.*, 557:9–23.
Law et al. (1986) "Use of Phosphotriester Synthetic Methods for Preparation of Phophatidylethanolamine–Analyte Conjugates" *Tetrahedron Letters*, 27:271–274.
Bruzik et al. (1986) "A General Method for the Synthesis of Glycerophospholipis" *J. Org. Chem.* 51:2368–2370.
Brigham et al. (1989) "Rapid Communication: In vivo Transfection of Murine Lungs with a Functioning Prokaryotic Gene Using A Liposome Vehicle" *Am. J. Med. Sci.* 298:278–281.

*Primary Examiner*—Deborah Crouch
*Attorney, Agent, or Firm*—McDonnell, Boehnen, Hulbert & Berghoff

[57] ABSTRACT

This invention herein describes pharmaceutical compositions and methods for targeted delivery of functional genes into cells and tissues in vivo. The invention discloses DNA:lipid complexes, methods of making such complexes and methods of using such complexes for facilitating the targeted delivery and entry of recombinant expression constructs into cells and tissues in vivo, and particularly delivery of such recombinant expression constructs to lung cells and tissues.

14 Claims, 13 Drawing Sheets

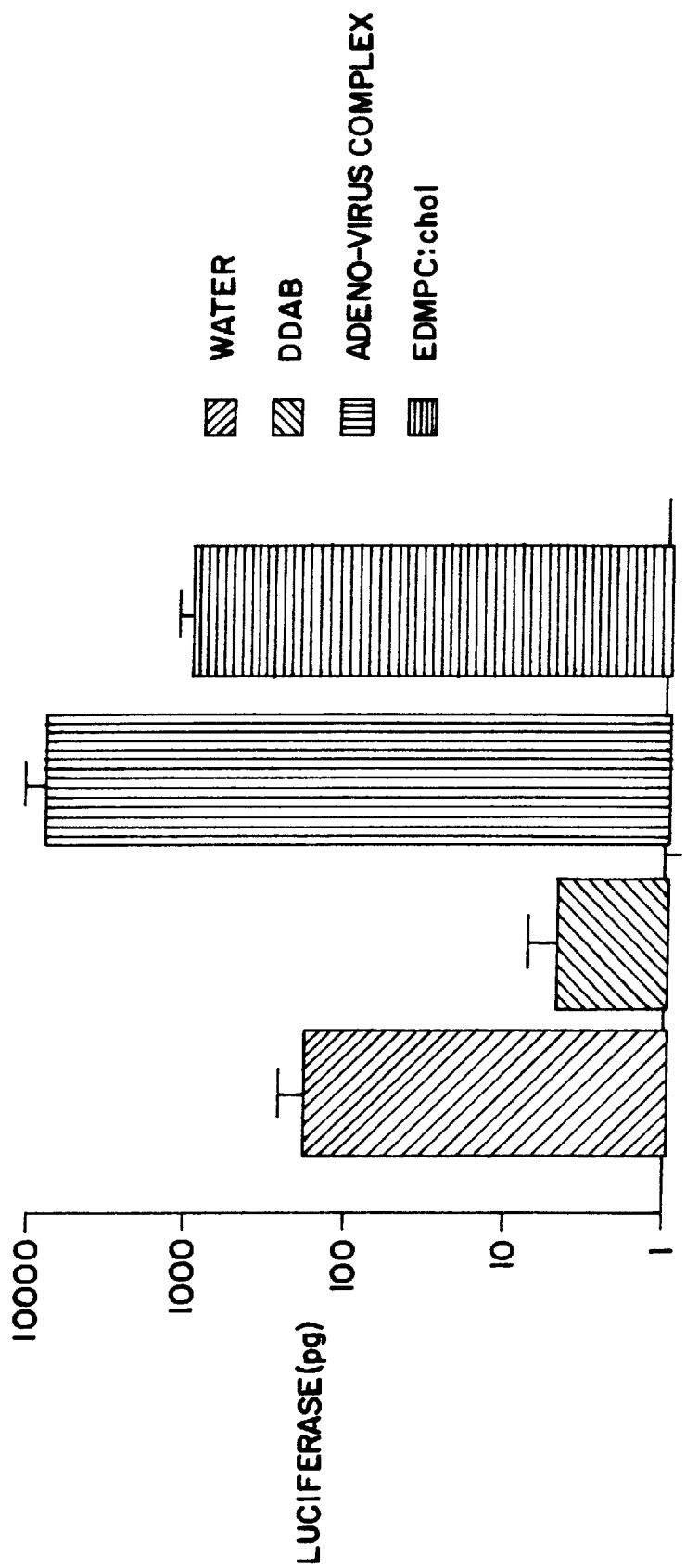

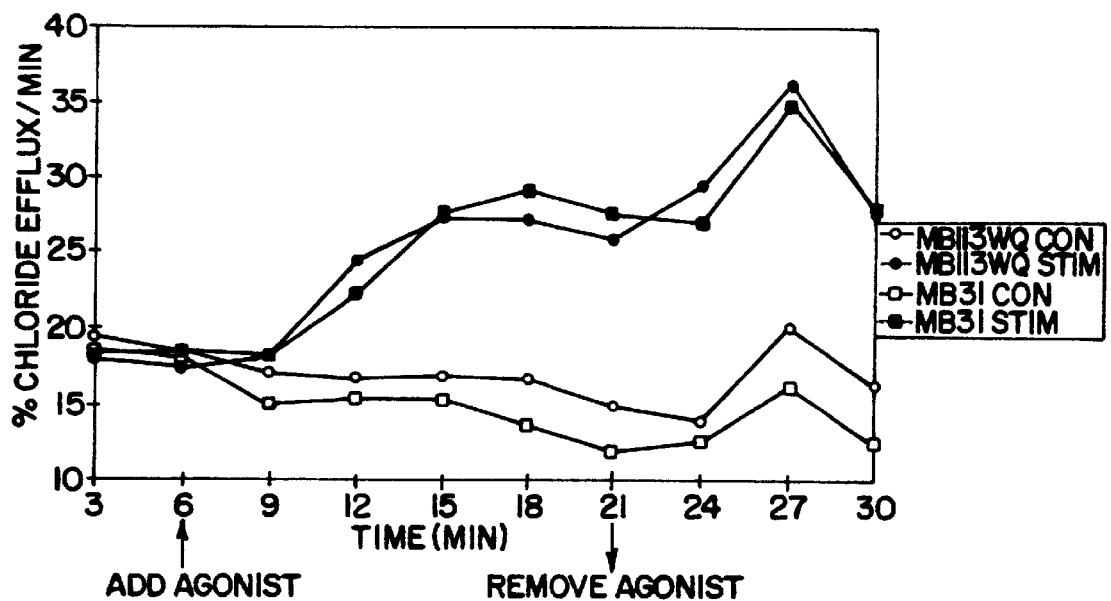
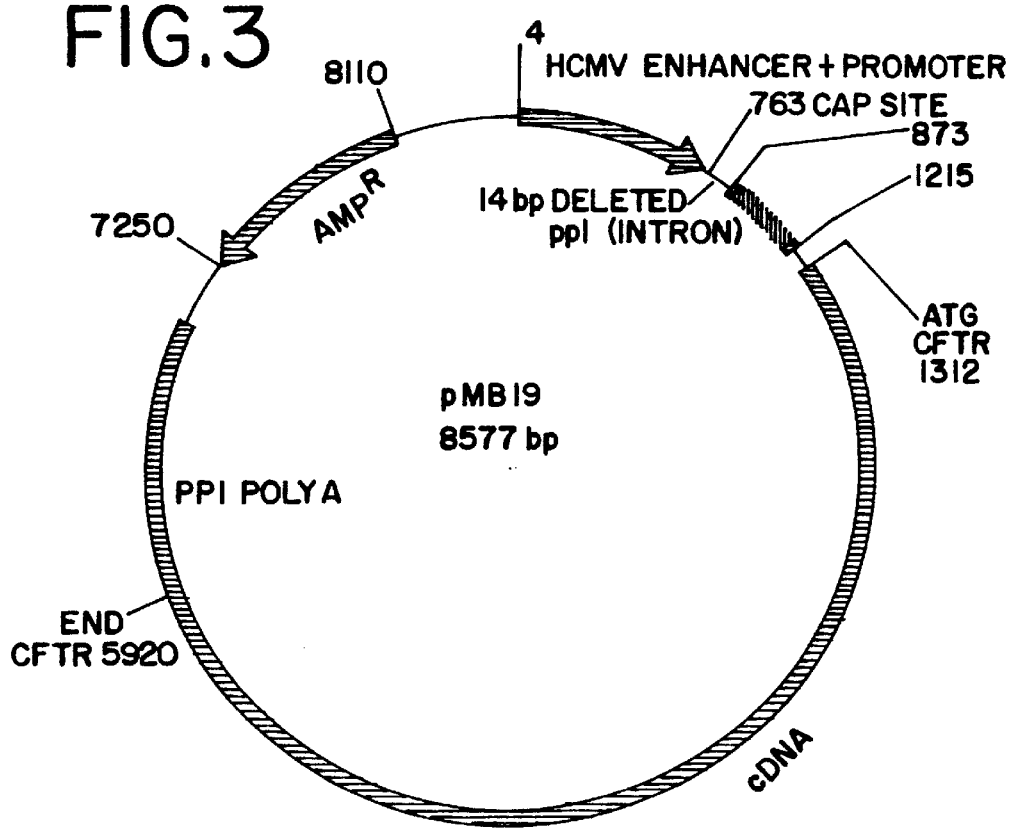

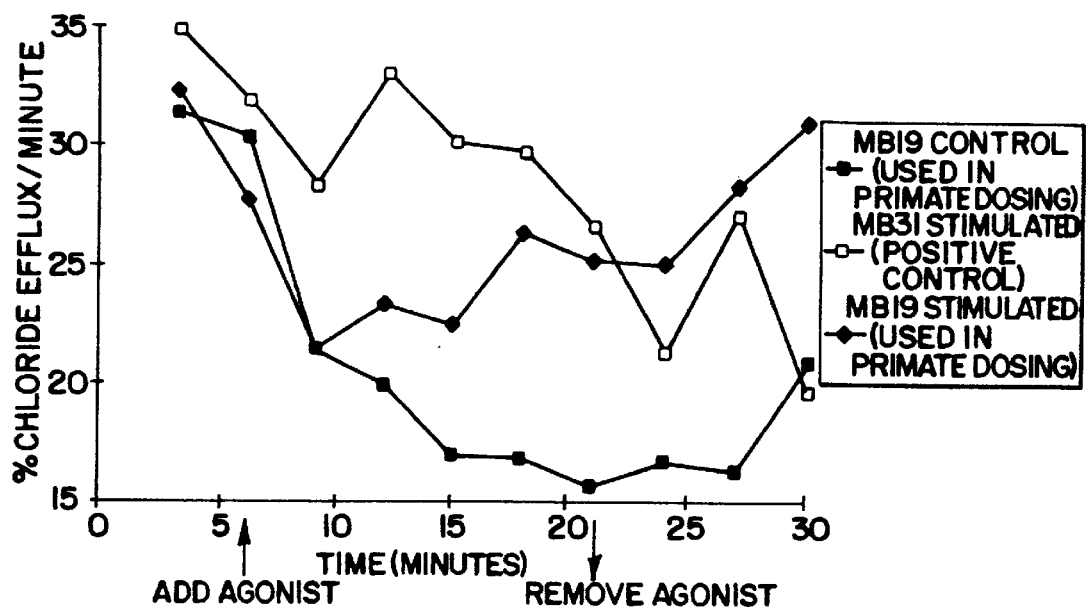
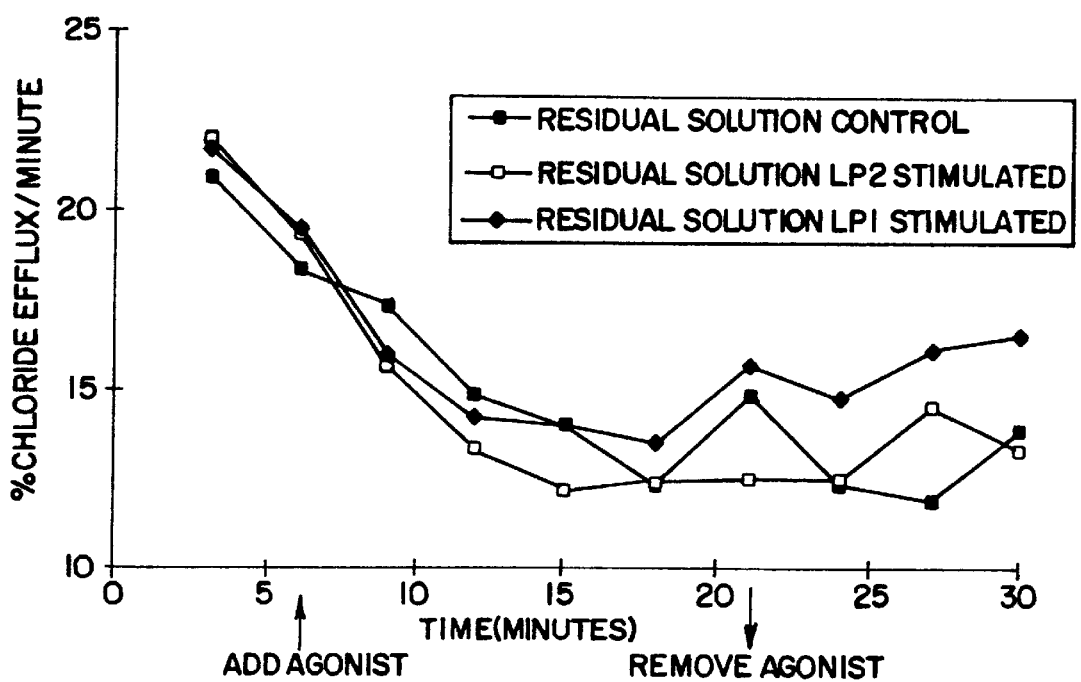

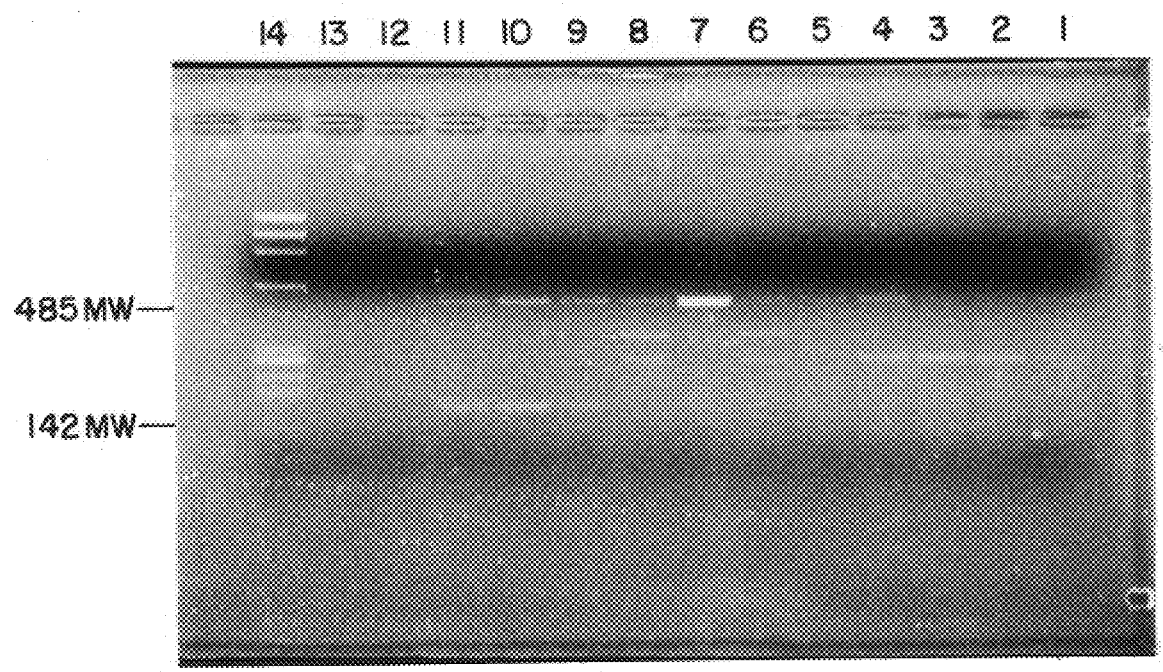

CATIONIC LIPID DNA COMPLEXES FOR GENE TARGETING

BACKGROUND OF THE INVENTION

1. Field of the Invention

A perennial goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. Recently, the advent of recombinant DNA technology and genetic engineering has provided the pharmacological arts with a wide new spectrum of agents that are functional genes carried in recombinant expression constructs capable of mediating expression of these genes in host cells. These developments have carried the promise of "molecular medicine", specifically gene therapy, whereby a defective gene could be replaced by an exogenous copy of its cognate, functional gene, thereby alleviating a variety of genetic diseases.

However, the greatest drawback to the achievement of effective gene therapy has been the inability in the art to introduce recombinant expression constructs encoding functional eukaryotic genes into cells and tissues in vivo. While it has been recognized in the art as being desirable to increase the efficiency and specificity of administration of gene therapy agents to the cells of the relevant tissues, the goal of specific delivery has not bee achieved in the prior art.

Liposomes have been used to attempt cell targeting. Rahman et al., 1982, Life Sci. 31: 2061–71 found that liposomes which contained galactolipid as part of the lipid appeared to have a higher affinity for parenchymal cells than liposomes which lacked galactolipid. To date, however, efficient or specific delivery has not been predictably achieved using drug-encapsulated liposomes. There remains a need for the development of a cell- or tissue-targeting delivery system.

Thus there remains in the art a need for methods and reagents for achieving cell and tissue-specific targeting of gene therapy agents, particularly recombinant expression constructs encoding functional genes, in vivo.

BRIEF SUMMARY OF THE INVENTION

The present invention is directed to an improved methods for targeted delivery of functional eukaryotic genes to cells and tissues in vivo. This delivery system achieves such specific delivery by the formation of DNA:lipid complexes between nucleic acid comprising a recombinant expression construct encoding a functional eukaryotic gene or fragment thereof complexed with a mixture of a cationic lipid and a neutral lipid. Methods of use are also provided. This invention has the specific advantage of targeted delivery of functional eukaryotic genes into cells in vivo, achieving effective intracellular delivery of constructs encoding functional genes more efficiently and with more specificity than conventional delivery systems.

In a first embodiment, the invention provides a pharmaceutical composition, comprising a formulation of a soluble complex of a recombinant expression construct and a mixture of a neutral lipid and a cationic lipid in a pharmaceutically acceptable carrier suitable for aerosol administration to an animal. In these embodiments of the invention, the recombinant expression construct comprises a nucleic acid encoding a protein, the nucleic acid being operatively linked to gene expression regulatory elements and whereby the protein encoded by the nucleic acid is expressed. In preferred embodiments, the recombinant expression construct encodes the human CFTR gene and is constructed to mediate efficient expression of the CFTR protein in lung epithelial cells.

In this first embodiment, the cationic lipid is a compound having formula I:

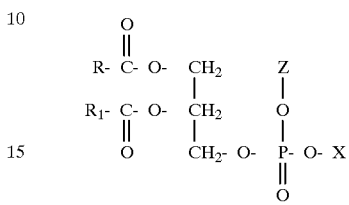

where Z is alkyl or alkylalkoxy, R and $R_1$ are independently straight-chain, aliphatic hydrocarbyl groups of from 11 to 29 carbon atoms, and X is a cationic moiety of formula

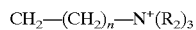

where n is an integer from 1 to 4 inclusive and each $R_2$ is independently hydrogen or lower alkyl. In preferred embodiments, the cationic lipid is O-ethyl-dimyristoylphosphatidylcholine. In additional preferred embodiments, the neutral lipid is either cholesterol or dioleoylphosphatidylethanolamine, and the O-ethyl-dimyristoylphosphatidylcholine and cholesterol or dioleoylphosphatidylethanolamine are present in the complex at a ratio of 1:1. Further preferred embodiments comprise a recombinant expression construct encoding human CFTR and a mixture of a neutral lipid and a cationic lipid comprises a ratio of DNA to lipid of 3:1 to 1:1. Particularly preferred are embodiments where the DNA comprising the recombinant expression construct is present in the complex at a concentration of about 0.5–2.5 mg/mL.

In a second embodiment, the invention provides a method for introducing a recombinant expression construct into a cell comprising lung tissue in an animal, the method comprising the step of administering the pharmaceutical composition of claim 1 to the animal as an aerosol that is inhaled by the animal. In preferred embodiments, the recombinant expression construct encodes the human CFTR gene and is constructed to mediate efficient expression of the CFTR protein in lung epithelial cells. In preferred embodiments, the cationic lipid is O-ethyl-dimyristoylphosphatidylcholine. In additional preferred embodiments, the neutral lipid is either cholesterol or dioleoylphosphatidtlethanolamine, and the O-ethyl-dimyristoylphosphatidylcholine and cholesterol are present in the complex at a ratio of 1:1. Further preferred embodiments comprise a recombinant expression construct encoding human CFTR and a mixture of a neutral lipid and a cationic lipid comprises a ratio of DNA to lipid of 3:1 to 1:1. Particularly preferred are embodiments where the DNA comprising the recombinant expression construct is present in the complex at a concentration of about 0.5–2.5 mg/mL.

Specific preferred embodiments of the present invention will become evident from the following more detailed description of certain preferred embodiments and the claims.

BRIEF DESCRIPTION OF THE DRAWINGS

FIG. 1 is a histogram showing a comparison of luciferase activity in mouse lung tissue treated with luciferase-encoding plasmids complexed with EDMPC-Cholesterol, DDAB, water or encapsulated within an adenovirus vector delivery system.

FIG. 2 is a graph of a comparison of chloride efflux in the presence and absence of stimuli in cells transfected with human CFTR-encoding plasmid vectors complexed with EDMPC:Cholesterol.

FIG. 3 is a schematic representation of the plasmid pMB19.

FIG. 4 is a graph of a comparison of chloride efflux in the presence and absence of stimuli in cells transfected with the human CFTR-encoding plasmid vectors pMB19 and pMB31 complexed with EDMPC:Cholesterol.

FIG. 5 is a graph of chloride efflux in cells transfected with residual trances of human CFTR-encoding plasmid vectors pMB19 and pMB31 DNA/EDMPC:Cholesterol complexes as described in Example 4.

FIGS. 6 through 8 are photographs of agarose gel electrophoretic analysis of PCR products.

DETAILED DESCRIPTION OF THE PREFERRED EMBODIMENTS

Figure 7:
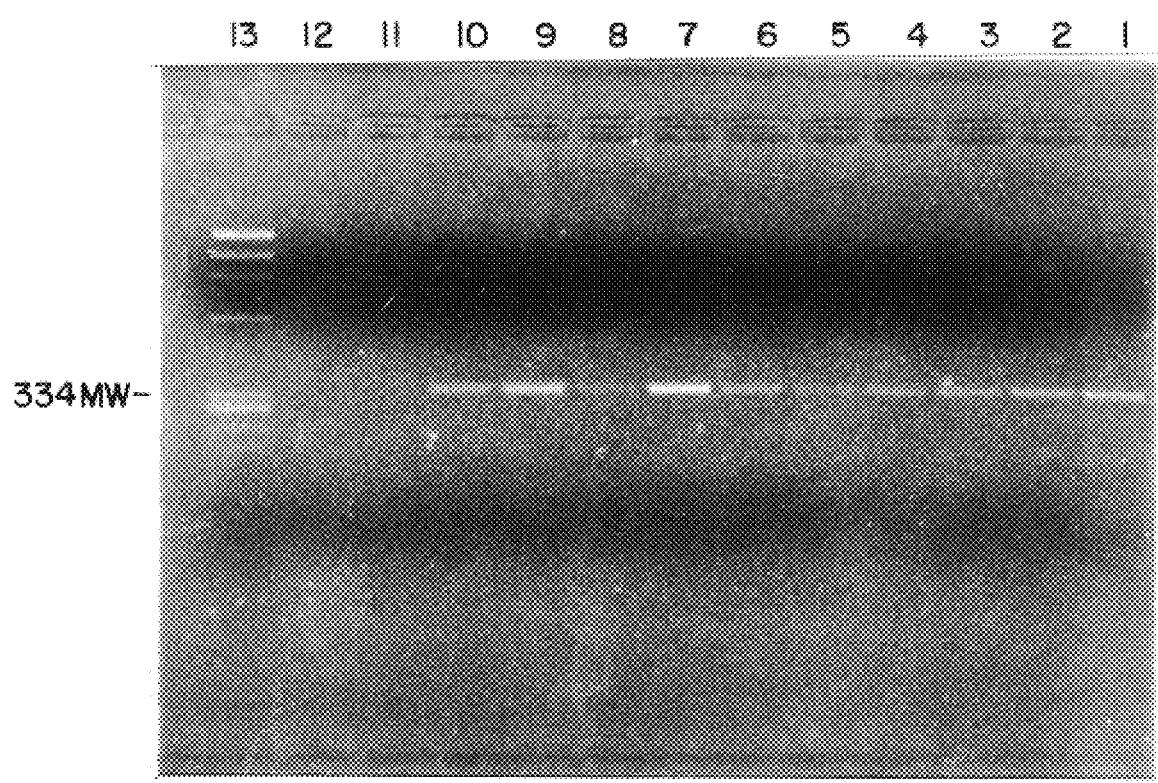

The present invention provides compositions of matter and methods for facilitating the entry into cells of nucleic acids, particularly recombinant expression constructs encoding functional eukaryotic genes. For the purposes of this invention, the term "recombinant expression construct" is intended to encompass a replicable DNA construct comprising a nucleic acid encoding a functional eukaryotic gene or fragment thereof, operably linked to suitable control sequences capable of effecting the expression of the gene in a suitable host cell. Expressly intended to fall within the definition of a "gene" are embodiments comprising cDNA and genomic DNA embodiments of functional eukaryotic genes, as well as chimeric hybrids thereof. Also intended to fall within the scope of the recombinant expression constructs of the invention are fragments of such genes which, when expressed, may inhibit or suppress the function of an endogenous gene in a cell, including, inter alia, antisense gene fragments.

In the recombinant expression constructs as provided by the present invention, the need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous or non-homologous recombination). Also useful are vectors which replicate autonomously in host cells. Suitable vectors will contain replicon and control sequences which are derived from species compatible with the intended expression host cell.

The recombinant expression constructs of the present invention are useful in gene therapy, and specifically, delivering exogenous copies of a defective gene to a specific tissue target in vivo. See generally Thomas & Capecchi, 1987, Cell 51: 503–512; Bertling, 1987, Bioscience Reports 7: 107–112; Smithies et al., 1985, Nature 317: 230–234.

The invention provides complexes of recombinant DNA constructs encoding functional eukaryotic genes or fragments thereof and also comprising a mixture of a cationic lipid and a neutral lipid. For the purposes of this invention, the term "cationic lipid" is intended to encompass lipids which are positively charged at physiological pH, and more particularly, constitutively positively charged lipids comprising, for example, a quaternary ammonium salt moiety. Expressly within the teachings of the present invention are co-owned and co-pending U.S. patent applications, Ser. Nos. 08/245,737, filed May 18, 1994; 08/248,005, filed May 24, 1994; 08/247,963, filed May 24, 1994; 08/157,637, filed June 7, 1994; and International Patent Application Nos. PCT/US94/13428, filed Nov. 17, 1994; PCT/US94/13363, filed Nov. 17, 1994; and PCT/US94/13362, filed Nov. 17, 1994, which are all herein incorporated by reference in their entireties.

Specifically, the cationic lipids of formula I are O-esters of the acidic diacylphosphatidyl compounds and may be produced therefrom. In the cationic lipids of formula I, each of R and $R_1$ together with the carboxyl group to which they are attached, are straight-chain, aliphatic, hydrocarbyl acid moieties of from 12 to 30 carbon atoms inclusive, preferably from 15 to 25 carbon atoms inclusive. Such acid moieties are commonly referred to as fatty acid moieties, and may be saturated or ethylenically unsaturated and within the cations of formula I R and $R_1$ are the same or are different. Illustrative moieties are lauroyl, myristoyl, palmitoyl, stearoyl, linoleoyl, tridecanoyl and oleoyl. In a modification where the cationic amphiphiles are prepared synthetically, it is advantageous for R and $R_1$ to be the same. Alteratively, when prepared from naturally occurring materials the R and $R_1$ moieties generally will be different.

Suitable Z groups are derived from alkanols or alkoxyalkanols which are straight-chain or branched. Illustrative Z groups include methyl, ethyl, propyl, isopropyl, n. butyl, sec-butyl, pentyl, hexyl, 2-methoxyethyl, 3-ethoxypropyl or 3-methoxypropyl. Preferred Z groups are straight-chain alkyl and more preferably the Z group is methyl or ethyl, especially ethyl.

Suitable X groups, illustrative by formula because of the complexity of the nomenclature include

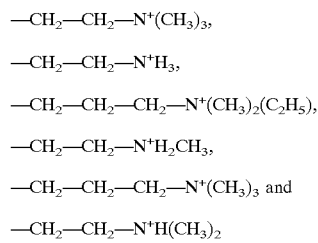

Preferred X groups are those wherein n is 1 and $R_2$ independently is hydrogen or methyl. Cationic amphiphiles wherein at least one $R_2$ is other than methyl are novel.

Cationic lipids are particularly useful as carriers for anionic compounds, particularly polyanionic macromolecules such as nucleic acids. As cationic lipids are positively charged, a tight charge complex can be formed between a cationic lipid carrier and a polyanionic nucleic acid, resulting in a lipid carrier-nucleic acid complex which can be used directly for systemic delivery to a mammal or mammalian cell. Where delivery is via aerosolization, the charge complex will withstand both the forces of nebulization and the environment within the lung airways and be capable of transfecting lung cells after the aerosolized DNA:lipid carrier complex has been deposited in the lung following intranasal or intraoral delivery of the aerosolized complex.

Neutral lipids are characterized in contrast to the cationic lipids of the invention and are characterized as being electrochemically neutral, although this definition does not preclude protonation of such lipids to produce a positively-charged salt under certain conditions. Expressly included within this definition are, inter alia, cholesterol and dioleylphosphatidyl ethanolamine.

Complexes of DNA and mixtures of cationic and neutral lipids of the invention are characterized by a number of parameters intrinsic to the formation of such complexes. These include the identity of the cationic lipid and the neutral lipid; the ratio of cationic lipid to neutral lipid; concentration of DNA in the complex; the ratio of DNA to lipid; DNA purity; cationic liposome size; the methods of preparing the DNA:liposome complexes; and other variables. Preferred combinations of cationic and neutral lipids include O-ethyl-dimyristoylphosphatidylcholine and cholesterol and O-ethyl-dimyristoylphosphatidylcholine and dioleylphosphatidyl ethanolamine. Preferred ratios of these lipids is 1:1. DNA concentration in the complexes is from about 0.5 mg/mL to about 5 mg/mL, more preferably from about 0.5 mg/mL to about 2 mg/mL. DNA:lipid ratios are preferably from 1:1 to about 3:1, most preferably about 1:1 to about 2:1. DNA purity has a direct effect on liposome complex formation, but DNAs having a purity of about 15% to about 90% are appropriate for complex formation.

The various lipid carrier-nucleic acid complexes wherein the lipid carrier is a liposome are prepared using methods well known in the art. Mixing conditions can be optimized by visual examination of the resultant lipid-DNA mixture to establish that no precipitation occurs. To make the lipid-DNA complexes more visible, the complexes that can be stained with a dye which does not itself cause aggregation, but which will stain either the DNA or the lipid. For example, Sudan black (which stains lipid) can be used as an aid to examine the lipid-DNA mixture to determine if aggregation has occurred. Particle size also can be studies with methods known in the art, including electronic microscopy, laser light scattering, Coulter™ counting/sizing, and the like. Standard-size beads can be included as markers for determining the size of any liposomes or aggregates that form. By "lipid carrier-nucleic acid complex" is meant a nucleic acid sequence as described above, generally bound to the surface of a lipid carrier preparation, as discussed below. The lipid carrier preparation can also include other substances or cofactors. Furthermore, the lipid carrier-nucleic acid complex can include targeting agents to deliver the complex to particular cell or tissue types. Generally, the nucleic acid material is added to a suspension of preformed liposomes which may be multi-lamellar vesicles (MLVs) or small unilamellar vesicles (SUVs), usually SUVs formed by sonication. The liposomes themselves are prepared from a dried lipid film that is resuspended in an appropriate mixing solution such as sterile water or an isotonic buffer solution such as 10 mM Tris/NaCl or 5% dextrose in sterile water and sonicated to form the liposomes. Then the preformed lipid carriers are mixed directly with the DNA.

Mixing and preparing of the lipid-DNA complex can be critically affected by the sequence in which the lipid and DNA are combined. Generally, it is preferable (to minimize aggregation) to add the lipid to the DNA at ratios of DNA:lipid from 6:1–5:1 through 1:1 inclusive (microgram DNA:nanomoles cationic lipid). Where the ratio of DNA:lipid is 1:4 or higher, better results are generally obtained by adding the DNA to the lipid. In either case, mixing should be rapidly achieved by shaking or vortexing for small volumes and by use of rapid mixing systems for large volumes. The lipid carrier and DNA form a very stable complex due to binding of the negatively charged DNA to the cationic lipid carriers. SUVs find use with small nucleic acid fragments as well as with large regions of DNA ($\geq 30$ kb).

In preparing the lipid carrier-nucleic acid complex for nebulization, care should be taken to exclude any compounds from the mixing solution which promote the formation of aggregates of the lipid carrier-nucleic acid complexes. Large particles generally will not be aerosolized by the nebulizer, and even if aerosolized would be too large to penetrate beyond the large airways. Aggregation of the lipid carrier-nucleic acid complex is prevented by controlling the ratio of DNA to lipid carrier, minimizing the overall concentration of DNA:lipid carrier complex in solution, usually less than 5 mg DNA/mL solution, and avoiding the use of chelating agents such as EDTA and/or significant amounts of salt, either of which tends to promote macro-aggregation. The preferred excipient is water, dextrose/water or another solution having low or zero ionic strength. Further, the volume should be adjusted to the minimum necessary for deposition in the lungs of the host mammal, while at the same time taking care not to make the solution too concentrated so that aggregates form. Increasing the volume of the solution is to be avoided if possible due to the need to increase the inhalation time for the host animal to accommodate the increased volume. In some cases, it may be preferable to lyophilize the lipid carrier-nucleic acid complexes for inhalation. Such materials are prepared as complexes as described above, except that a cryoprotectant such as mannitol or trehalose is included in the buffer solution which is used for preparation of the lipid carrier-DNA complexes. Any glucose generally included in such a buffer is preferably omitted. The lipid carrier is rapidly freeze-dried following mixing of the lipid and DNA. The mixture can be reconstituted with sterile water to yield a composition which is ready for administration to a host animal.

Liposomes of the invention may be sized in accordance with conventional techniques, depending upon the desired size. In some instances, a larger liposome injected into the bloodstream of an animal has higher affinity for lung cells as compared to liver cells. Therefore, the particular size range may be evaluated in accordance with any intended target tissue by administering lipid-nucleic acid complexes of varying particle sizes to a host animal and determining the size of particle which provides the desired results.

The DNA:lipid complexes of the invention have utility in mediating the efficient delivery of the recombinant expression constructs of the invention, encoding functional genes or fragments thereof, into eukaryotic, preferably mammalian, most preferably human cells. DNA:lipid complexes of the invention are useful for achieving gene transfer in vitro using established techniques. More importantly, the DNA:lipid complexed provided by this invention, and the methods of administering the DNA:lipid complexes provided herein, are capable of specifically delivering recombinant expression constructs of the invention to particular tissues and cells comprising those tissues in vivo, thereby providing targeting of these genes to specific tissues. These properties of the pharmaceutical compositions and methods of the present invention provide for real gene therapy, whereby a particular deficient gene is restored by the introduction of a functional copy of the normal cognate gene into the cells of the affected tissue, without deleterious and unpredictable results from inappropriate introduction of the construct into other cells and tissues of the body nonspecifically. In a particular embodiment, the present invention provides methods of pharmaceutical compositions for introducing a recombinant expression construct encoding the human cystic fibrosis transmembrane regulator (CFTR) gene into lung cells in vivo.

Thus, the invention provides methods and pharmaceutical compositions having a number of advantages over the prior art. The liposomes and lipid complexes of the invention have been extensively studied in humans, and are non-immunogenic, relatively non-toxic, and non-infectious. Recombinant expression constructs of any practicable size can be used, there being no limitation on large plasmid size due to the absence of packaging the DNA into the genome of a vector organisms like a retrovirus or an adenovirus. Gene transfer can be achieved in non-dividing cells, unlike prior art systems which relied on viral vectors whose life cycle required the infected cells to be dividing. In addition, the specific formulation of the DNA:lipid complexes of the invention can be altered to affect targeting and duration of the gene-expression effect. The DNA:lipid complexes of the invention are also amenable to many delivery routes, and are less likely to encounter the types of severe regulatory requirements anticipated for viral-based delivery systems.

The DNA:lipid complexes of the invention have the advantage that the efficiencies of delivery are comparable with known prior art delivery systems. FIG. 1 illustrates a comparison of the efficiency of delivery of a recombinant expression construct encoding firefly luciferase into mouse trachea using DNA:lipid complexes of the invention (EDMPC:chol) and an adenovirus-based vector system (Adeno-virus complex).

The DNA:lipid complexes of the invention may be administered to an animal to effect delivery of functional genes into specific tissues by any appropriate therapeutic routine, including intravenous, intraperitoneal, subcutaneous, or intramuscular injection; direct injection into the target tissue(s); or, most preferably for the present invention, by aerosol delivery to the lung, using a nebulizer or other aerosol-producing device.

The methods and pharmaceutical compositions of the invention thus are particularly useful and appropriate for introducing functional human genes, particularly human CFTR, to lung tissue. These methods and pharmaceutical compositions thus have utility in the treatment of human diseases, including cystic fibrosis and chronic bronchitis.

The following Examples illustrate certain aspects of the above-described method and advantageous results. The following examples are shown by way of illustration and not by way of limitation.

EXAMPLE 1

Preparation of EDMPC:Cholesterol (1:1) Small Unilamellar Vesicles

To a 1 L round bottom flask was added 500 μmoles cholesterol dissolved in an excess of chloroform and then 500 μmoles EDMPC were also dissolved in an excess of chloroform. The amount of EDMPC was determined by phosphorus assay and not simply on the basis of the dry weight of the reagent.

After brief, gently mixing, the flask was attached to a rotary evaporating apparatus and chloroform withdrawn under slow speed and water vacuum conditions until almost all of the solvent was evaporated. Evaporation was completed at maximum rotation speed using a vacuum pump to completely dry the lipid mixture to a thin film on the wall of the round bottom flask.

As an intermediate step to the formation of the title composition, multilamellar vesicles (MLVs) were prepared from this film by the addition of 16 mL endotoxin-free water to the flask, which was then warmed to 37° C. in a water bath with gentle hand-swirling. The MLVs thus formed were removed from the flask using a 9" Pasteur pipette and transferred to a 20 mm screw cap tube at room temperature. The flask was cleared of any remaining MLVs by washing with an additional 4 mL endotoxin-free water, which was added to the 16 mL previously transferred from the flask. These solutions were mixed, and aliquotted equally into 20 16 mL screw cap tubes using a Pasteur pipette.

MLVs were converted into the SUVs of the title composition by sonication. Each of the 16 mL screw cap tubes containing MLVs were placed individually into a sonicating water bath maintained at 36° C. for 5 min, and the temperature of the bath checked between the introduction of each tube. Sonicated droplets within each tube were collected by brief vortex mixing, and the individual solutions of SUVs were then combined into a single 20 mm screw cap tube using a 9" Pasteur pipette, and then filtered using a 0.2 micron disposable filter (Nalgene). Finally, an amount of an endotoxin-free solution of 25 % dextrose in water, equal to one-quarter of the final volume of SUVs, was added to the tube of SUVs. This resulted in a suspension of SUVs comprising 20 mM EDMPC and 20 mM cholesterol (40 mM total lipid) in a 5 % dextrose solution, which was kept at 4° C. until use.

EXAMPLE 2

Large Scale Plasmid DNA Preparation

Plasmid DNA was prepared in large-scale (i.e., milligram) quantities using a modification of the alkaline lysis procedure (Sambrook et al., 1990, ibid.). Briefly, bacteria comprising a single colony were grown for 12–18 hours or overnight in 15 mL TB broth (47 g/L TB (Sigma Chemical Co., St. Louis, Mo.)/8% glycerol) supplemented with 100 μg/mL carbenicillin at 37° C. with shaking (250 rpm). 2–2.5 mL of this culture was then added to 400 mL TB (supplemented with 100 μg/mL carbenicillin) in each of six 2 L flasks (for a total of 2.4 L culture) and grown at 37° C. with shaking overnight (16–18 h).

After overnight growth, bacteria were collected by centrifugation for 10 min. at 4° C. in a Beckman J2-MI centrifuge equipped with a JA-10 rotor. The bacterial pellet in each centrifuge bottle was gently resuspended in 20 mL of an ice-cold solution of 50 mM dextrose in 25 mM HCl buffer (pH8)/10 mM EDTA. To the resuspended bacterial cell pellets were added 40 mL of a freshly-made solution of 0.2 N NaOH/1% sodium dodecyl sulfate at room temperature, resulting in cell lysis upon gentle agitation of this mixture on ice for about 5 min. After the added lysis solution has been thoroughly mixed into the bacterial suspension and the cells lysed, the mixture was allowed to stand at room temperature for 5 min. To this mixture of lysed bacteria was added 20 mL of an ice-cold solution of 3 M potassium acetate, which was mixed into the lysed bacterial solution gently by hand and then stored on ice for 10 min.

A flocculate white precipitate formed, comprising bacterial chromosomal DNA, RNA and SDS/protein/membrane complexes, which were cleared from the solution by centrifugation at 800 rpm for 15 min at 4° C. in the JA-10 rotor as above.

After centrifugation, the supernatant was transferred with filtering through Miracloth to 250 mL centrifuge bottles, and 50 mL isopropanol added at room temperature, mixed and incubated for 10 min. The plasmid DNA precipitate was recovered by centrifugation at 5000 rpm for 10 min at room temperature in a JA-14 rotor (Beckman). The alcohol-containing supernatant was decanted and residual supernatant removed by vacuum aspiration.

The plasmid DNA pellets were resuspended in 6 mL of a solution of 6 mM Tris-HCl (pH8) and transferred to 50 mL centrifuge tubes upon dissolution. To each tube was added and equal volume of cold (−20° C.) 5 M LiCl, the solutions mixed by hand and then centrifuged at 8000 rpm for 10 min at room temperature in a JA-20 rotor (Beckman). The supernatant solution from each tube was transferred to a fresh tube and the plasmid DNA then re-precipitated by the addition of an equal volume of isopropanol, mixed and collected by centrifugation at 5000 rpm for 10 min at room temperature in a JA-20 rotor. The alcohol-containing supernatant solution was then decanted, residual alcohol removed by aspiration, and the plasmid DNA pellets allowed to air dry for 5 min.

Contaminating bacterial RNA was removed from the plasmid DNA by dissolving the pellets in 1 mL 10 mM Tris-HCl (pH8), adding about 0.5–0.75 µg of pancreatic RNase per mL, followed by incubating the mixture at 37° C. for 1 h. Disappearance of RNA was determined by ethidium bromide-stained agarose gel analysis (see Sambrook et al., ibid.).

Plasmid DNA was purified by phenol-chloroform extraction. Briefly, to each aliquot of plasmid DNA solution was added an equal volume of Tris-saturated phenol:chloroform (1:1), the immiscible solutions mixed by vortexing, and centrifuged in a laboratory tabletop microfuge for 5 min at room temperature. The aqueous (upper) layer was removed, transferred to a fresh microfuge tube, and extraction with phenol:chloroform repeated at least twice. These extractions were followed by two extractions of the aqueous layer with Tris-saturated chloroform. Plasmid DNA was concentrated by precipitation, with the addition of 5 M sodium acetate to a final concentration of 0.3 M and the addition of two volumes of cold (−20° C.) absolute ethanol. DNA was allowed to precipitate in this solution at −20° C. for 1 h or overnight.

After precipitation, plasmid DNA was collected by centrifugation at about 600 rpm in a clinical microcentrifuge. The alcohol-containing supernatant was aspirated by vacuum, and the pellet washed twice with 70% ethanol/water (4° C.). The washed pellets were air dried for at least 30 min. Plasmid DNA pellets were dissolved in a total of 6 mL of a solution of 10 mM Tris-HCl (pH8), and concentration determined by spectrophotometric analysis of a 1-to-200 dilution of the recovered plasmid at $A_{260}$.

EXAMPLE 3

Preparation of DNA:Liposome Complexes

EDMPC:Cholesterol:Plasmid DNA liposomes were prepared as follows. An EDMPC:Cholesterol mixture (1:1, 20 µmoles/µL) was prepared as described in Example 1 above. Complexes with plasmid DNA were prepared in DNA:liposome ratios of 1:1 and 2:1; in preliminary experiments, unsuitable precipitates were observed to occur when DNA and lipid were mixed at ratios of 1:2 to 1:5. DNA and EDMPC: Cholesterol were each first brought from storage conditions (−20° C. for DNA, 4° C. for liposomes) to room temperature before use over the course of about 1.5 h. DNA concentration in the liposome preparations were optimally 1000 µg/mL complex (for ratios of 2:1 DNA:liposomes) and 2000 µg/mL complex (for ratios of 1:1 DNA:liposomes). DNA concentrations were typically determined just prior to DNA:liposome complex formation, by ultraviolet spectrophotometry as described in Example 2. EDMPC:Cholesterol mixtures were typically used at a concentration of 40 µmole/mL total lipid, equivalent to 20 µmoles/mL EDMPC and 20 µmoles/mL cholesterol.

DNA:liposome complexes were prepared from these reagents as follows. Each component was prepared in individual microfuge tubes to a total volume per tube of 500 µL. An appropriate amount of DNA (equivalent to a final DNA concentration of 1000 µg DNA/mL complex) was added to one tube, and brought to volume with water or a solution of 5% dextrose in water. The appropriate amount of the EDMPC:Cholesterol mixture (500 nmoles lipid/1000 µg DNA at a 2:1 ratio; 2000 nmoles lipid/2000 µg DNA at a 1:1 ratio) was added to a second tube, and water or a solution of 5% dextrose in water was added to bring this solution to a total volume of 500 µL. Each tube was mixed by vortexing for 15 sec. The contents of the lipid mixture-containing tube were then added to the DNA-containing tube using a 1 mL automatic pipettor. It was found that it was essential that this addition was performed slowly, in a constant stream, to the top of the DNA solution in tube A. As the lipid solution mixed with the DNA, formation of the DNA:liposome complex was detected by the solution becoming slightly cloudy and opalescent. It was also determined that, at this stage, the mixture could not be vigorously mixed (for example, by vortexing) without seriously compromising the integrity and usefulness of the complexes so formed.

After the complexes were formed, the final concentration of DNA was determined by ultraviolet spectrophotometry as described above, and the size of the DNA:liposome complexes determined by light scattering measured at 400 nm.

EXAMPLE 4

Detection of Functional CFTR Expression in Transfected Cells Using a Chloride Efflux Assay A chloride ion efflux assay was used to detect functional expression of CFTR in transfected cells.

About 24 h prior to introducing CFTR into cells, cells were split into a 6-well tissue culture dish, each well receiving 1 mL of 10 mL of the cells on the dish and 3 mL media. Cells were returned to the incubator and allowed to grow overnight at 37° C./5% $CO_2$, or until they were about 70–80% confluent. For assay, media were removed from the wells and each well was washed with 2 mL serum-free media. 1 mL of serum-free media was then added per well, and the cells incubated at 37° C. for 1–2 h. 200 µl of a DNA-lipid complex comprising a recombinant expression construct encoding CFTR were then added to each well and incubated at 37° C. for 6–8 h. After this incubation, media were removed from each well, the wells were washed twice with 2 mL serum-free media and incubated in 4 mL serum-containing media at 37° C. for 48 h.

The chloride ion efflux assay was performed as follows. Media were aspirated from each of the wells containing cells treated with DNA-lipid complexes, and washed twice with efflux solution (135 mM NaCl/2.4 mM $K_2HPO_4$/0.6 mM $KH_2PO_4$/1.2 mM $CaCl_2$/1.2 mM $MgCl_2$/10 mM glucose/10 mM HEPES (pH 7.4)). Cells were then incubated with 1 mL efflux solution containing $Na^{36}Cl$ at a final concentration of 2.5 μCi/mL $^{36}Cl^-$ for 2 h at 37° C. After incubation, the $^{36}Cl^-$-containing efflux solution was aspirated from the cells and the cells then washed each of 4 times with 1 mL efflux solution. The cells were then incubated with 1 mL efflux solution for 3 min at room temperature, and the efflux solution then removed from the cells and transferred into a scintillation vial containing 5 mL scintillation cocktail. A fresh aliquot of efflux solution was added to each well and incubated for an additional 3 min. After each incubation, efflux solution was transferred to a scintillation vial containing 5 mL scintillation cocktail, and a fresh 1 mL aliquot of efflux media was added to the cells and incubated for 3 min. These steps of the assay were repeated ten times for a total of 30 min. In certain of the wells, $^{36}Cl^-$ ion efflux was stimulated by incubating these cells in the presence of 40 μM Forskolin (Sigma), 500 μM cpt-cAMP (Sigma), and 100 μM IBMX (Sigma) in efflux solution, efflux being stimulated at repetitions 3 through 7.

The extent of $^{36}Cl^-$ ion efflux over this period was determined by scintillation counting, and the basal rate of $^{36}Cl^-$ ion efflux compared with the rate of efflux in cells stimulated by Forskolin/cpt-cAMP/IBMX. Extent of efflux was normalized relative to the amount of $^{36}Cl^-$ ion remaining inside the cells after the 30 min incubation. This quantity was determined by lysing the cells by incubating them with 1 mL of scintillation fluid for 15 min. The lysate from each well was then transferred into a scintillation vial, the well washed with 1 mL of efflux solution which was added to the cell lysate, and the $^{36}Cl^-$ ion-associated radioactivity counted.

The results of one such assay are shown in FIG. 2. Two plasmids encoding CFTR and differing in the details of the construct (see Table I) were tested with (closed circles and boxes) and without (open circles and boxes) stimulation. As is shown in the Figure, stimulation results in the rapid induction of chloride ion efflux over the basal rate of efflux, which efflux persists even after the stimulus is removed (time points 24–30). These results demonstrate the utility of this assay to detect functional expression of CFTR in heterologous cells, and thus forms an in vitro standard for determining the vigor of different recombinant expression constructs in expressing human CFTR.

EXAMPLE 5

Functional Delivery of Human CFTR to Primate Lung Cells In Vivo

Functional delivery of human CFTR into primate lung cells in vivo was demonstrated using DNA:lipid complexes of CFTR-encoding plasmid DNA (see Table 1) complexed with EDMPC:Cholesterol. Two rhesus monkeys were administered DNA/Lipid complexes by aerosol containing EDMPC lipid and hCFTR DNA complexes. The animals were euthanized 72 hours post-treatment and their respiratory airways evaluated for hCFTR expression. Rhesus monkeys were used for the simplicity of aerosol administration as well as their similarity to human lung physiology.

Two male rhesus monkeys (*Macaca mulatta*) were used. These primates were colony born at University of California, Davis Primate Research Center and examined prior to study start by a primate center veterinarian and were found to be in good health by clinical examination and laboratory studies. The animals weighed between 5.7 and 6.7 kg and each were administered Ivermectin (a parasiticide) at study start. Animals were individually housed during the study and lightly anesthetized before administration and necropsy. Animals were handled according to the NIH guide for the care and use of research animals.

Dosing of the animals was performed and necropsies done 72 hours post-administration. A MiniHEART nebulizer was used for the aerosol generation which was delivered via a tight-fitting face mask. Ten to 20 mL of DNA/lipid complexes were transferred to the nebulizer for each animal. Details of the experimental protocol are summarized in Table II below. Blood samples for clinical pathology and blood gas determinations were taken following anesthesia just prior to euthanasia. Animals were necropsied immediately following euthanasia. Harvested tissues and observations were confined to the respiratory tract.

TABLE I

Vectors with the CFTR cDNA

| | enhancer | promoter | intron | polyA | antibiotic |
|---|---|---|---|---|---|
| MB19: | HCMV | HCMV | ppi | ppi | amp |
| MB31: | HCMV | HCMV | ppi | SV40 | amp |
| MB6S: | HCMV | HCMV | ppi Nmyc | ppi | amp |
| MB66: | HCMV | HCMV | ppi Cmyc | SV40 | amp |
| MB76: | HCMV | HCMV | ppi | 3xSV40 | amp |
| MB77: | — | CC10 | ppi | 3xSV40 | amp |
| MB78: | HCMV | CC10 | ppi | 3xSV40 | amp |
| MB81: | — | CFTR | ppi | 3xSV40 | amp |
| MB87: | HCMV | CFTR | ppi | 3xSV40 | amp |
| MB90: | HCMV | HCMV | — | 3XSV40 | amp |
| MB93: | HCMV | HCMV | pgl3 | SV40 | amp |
| MB97: | HCMV | HCMV | pgl3 | SV40 | amp/tet |
| MB113: | HCMV | HCMV | pgl3 | SV40 | tet |

TABLE II

| | Animal MMU25464 | Animal MMU25744 |
|---|---|---|
| Weight at Dosing (kg) | 6.76 | 6.26 |
| Time Period of Dosing (minutes) | 150 | 84 |
| Ventilation Fraction | 39% | 37% |
| Inhaled volume (L) | 92.1 | 45.8 |
| Aerosolized Liquid Total (mL) | 15.3 | 10.1 |
| Lung Deposition (65% of total liquid)* (mL) | 3.1 | 1.8 |
| Dosage (mL/kg) | 0.46 | 0.29 |

*calculated volume

The cationic lipid, 1,2-dimyristoyl-sn-glycero-3-ethylphosphocholine, chloride salt (EDMPC, obtained from Avanti Polar Lipids, Inc., Alabama) was used to produce the DNA:lipid complexes used for aerosol administration. Liposomes were prepared by sonication of EDMPC and cholesterol (Sigma, Missouri) at 1:1 ratio as described above in Example 1. Preliminary testing of liposomes was done using a beta-galactosidase-encoding recombinant expression construct (pMB10; see Table I) for evaluation of the competency of these liposomes for in vitro transfection assay before making the dosing solution. These results showed that these EDMPC liposomes resulted in efficient gene delivery when complexed with DNA (data not shown).

CFTR-encoding plasmid DNA (pMB19; Table I) was used for complexing with these liposomes. The expression vector pMB19 contains the human cytomegalovirus (HCMV) promoter, the 5' prepro-insulin intron, hCFTR cDNA, and the prepro insulin polyadenylation signal (see FIG. 3). The vector also contains an ampicillin resistance gene for propagation in bacteria. Plasmid DNA was purified by alkaline lysis and phenol/chloroform extraction as described above in Example 2. HPLC analysis of plasmid DNA purity showed that these plasmid DNA preparations were between 13 and 27% pure plasmid DNA.

The dosing solution was comprised of DNA/lipid complexes containing EDMPC:cholesterol liposomes and the hCFTR expression vector pMB19 at a 2:1 DNA:lipid ratio with a DNA concentration of 1 mg/mL. Complexes were prepared as described in Example 3 above. A sample of each DNA/lipid complex was retained for evaluation in the chloride efflux assay to ensure potency, as described in Example 4 above. The results of this assay showed that the complexes were competent to produce functional hCFTR expression (see FIG. 4). This assay was also used to evaluated the residual material remaining in the nebulizer after administration to the animals. This material was found to produce little if any efflux response (see FIG. 5).

Animals were necropsied immediately following euthanasia 72 hours post-administration. Gross observations showed no significant lesions in any of the organ systems examined for animal MMU25744. Histological examination of animal MMU25744 showed a very mild pulmonary hemorrhage which appeared to be of the type associated with pulmonary hypertension. A lung mite infection appears to have caused peribronchiolitis. Gastrointestinal lesions seen were similar to those commonly seen in the UC Davis colony of animals. A very mild, multifocal acute hemorrhage in brainstem/cervical spinal cord appears to be associated with euthanasia. No other clinically significant effects were seen.

Animal MMU25464 (the higher does animal) had extensive hemorrhage involving the dorsal one-third of the right and left lungs. This hemorrhage extended into the parenchyma and was moderately more pronounced in the caudal lung lobes. Clotted blood partially filled the trachea and primary bronchi and the lungs failed to collapse. Total white cell count and blood gas determinations taken just prior to necropsy were normal, however, and the animal showed no signs of unusual clinical behavior. Similar to animal mMU25744, animal MMU25464, was observed to have granulomatous peribronchitis caused by lung mites, ischemic necrosis in the myocardium associated with euthanasia, and gastrointestinal lesions common to colony animals. Histological examination of regions demonstrated the accumulation of significant quantities of erythrocytes in airways and alveolar spaces. These were not accompanied by the presence of increased numbers of inflammatory cells nor any evidence of erythrophagocytosis. No other significant histological changes were recognized.

Samples for CFTR analysis were taken from the following tissues: pharynx, esophagus, mediastinal lymph node, trachea, right and left anterior lung lobe, right and left middle lung lobes, right and left caudal lung lobes, and right azygos lung lobe. The tissues were prepared as required for the assays designed to monitor delivery and expression of the pMB19 DNA described below. Tissues from two untreated primates were analyzed coincidentally with the transfected animals. These controls included a primate of the same species as well as from a different species (*Macaca fasicularis* for immunohistochemistry and *Macaca nemistrina* for in situ RT-PCR). Additional tissues were collected from treated animals for routine histological evaluation.

CFTR expression was assayed using a reverse transcriptase polymerase chain reaction assay (RT-PCR) on whole tissues. These assays were performed using vector specific primers and CFTR specific primers. The vector specific primers used were:

| | |
|---|---|
| 5' AGA TCG CCT GGA GAC GCC AT 3' | forward primner (3651–3671 bp in pMB19) |
| and | |
| 5' GCT CCT AAT GCC AAA GGA AT 3' | reverse primer (1246–1266 bp in pMB19, upstream from hCFTR ATG site). |
| The CFTR specific primers were used: | |
| 5' CCT GTC TCC TGG ACA GAA A 3' | forward primer (3337–3355 bp in pMB19) |
| and | |
| 5' GTC TTT CGG TGA ATG TTC TGA C 3' | reverse primer (3651–3671 bp in pMB19). |

Tissues were frozen on dry ice for RT-PCT and stored at −70° C. Tissue samples were homogenized and used directly in this evaluation.

Briefly, RT-PCR was performed by preparing first-strand cDNA from cellular RNA isolated from frozen tissues using standard techniques (see Sambrook et al., ibid.), including specifically the use of random hexamer for priming and MMLV-derived reverse transcriptase. cDNA was used in PCR reactions performed as follows. The entire 25 μL of the first-strand cDNA reaction was mixed with the components of the PCR reaction (under standard conditions; see Innis et al., 1990, *PCR Protocols: A Guide to Methods and Applications,* Academic Press, New York), including 25 μM apiece of each of the specific pairs of PCR primers. PCR reactions were overlayed with light mineral oil to prevent condensation and then subjected to the following PCR cycling protocol:

| | |
|---|---|
| 1 cycle | 10 min 94° C. |
| 30 cycles | 1 min 94° C. |
| | 2 min 55° C. |
| | 3 min 72° C. |
| 1 cycle | 10 min 72° C. |
| | 2 min 27° C. |

After completion of the reaction, the apparatus was programmed to take and hold the reaction mixtures at 4° C.

Results of these assays are shown in FIG. 6. In these assays, the vector specific primers were expected to yield a band representative of plasmid DNA (485 bp) and a hCFTR RNA-specific band (142 bp). The results shown in FIG. 6 revealed the expected plasmid DNA band but not the RNA band. Other bands are also present which appear to be due to non-specific priming.

Figure 8:
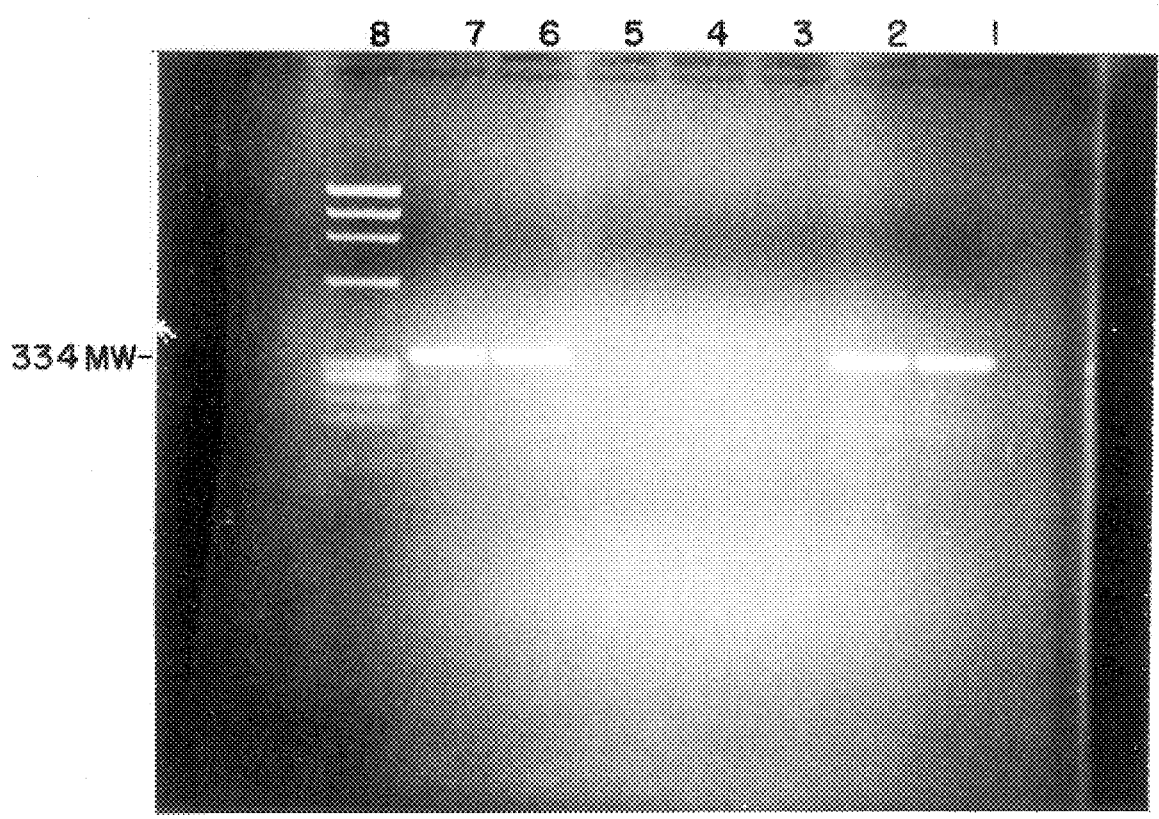

The use of vector-specific primers was approximately 4-fold less sensitive in detection of hCFTR RNA than the CFTR specific primers. Therefore, RT-PCR was also performed on all tissues using the CFTR specific primers. In these experiments, a band of the expected size (334 bp) was present in both the treated and untreated tissues (FIGS. 7 and 8). The intensity of this band was diminished when the untreated tissue samples were treated with DNase (data not shown). This decrease in the intensity of the band following DNase treatment indicated that the produced DNA fragment was, in part, due to PCR amplification of endogenous primate genomic DNA sequences, which produce a DNA fragment of the appropriate size even in the control (untreated) animals. The minor band which remains in the untreated tissues after DNase treatment is removed by RNA treatment and reflects the very low level of endogenous CFTR transcription present in the control animals.

In situ RT-PCR was also performed using the CFTR specific primers as described above. Tissues were paraformaldehyde fixed, paraffin embedded and sectioned for in situ RT-PCT, using a slight modification of the procedure described by Nuovo (1992, *PCR in situ Hybidization: Protocols and Applications,* Raven Press, New York), hereby incorporated by reference herein.

Figure 9:
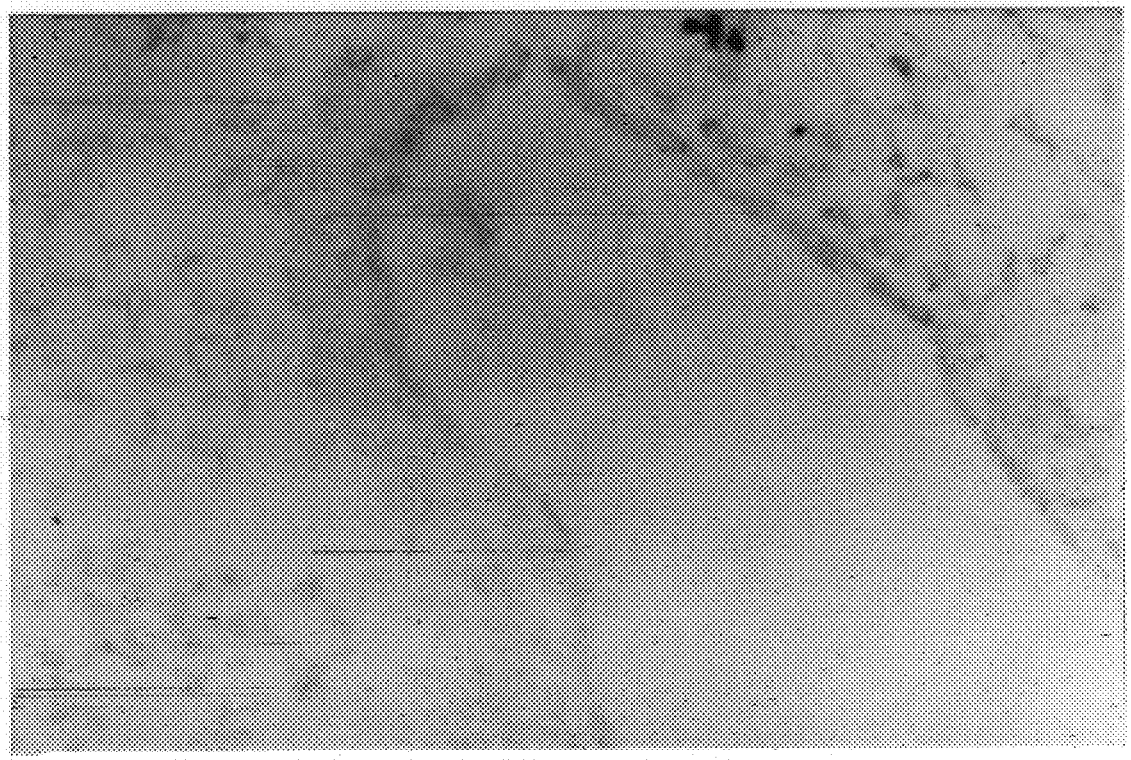
FIGS. 9 through 12 are photographs of in situ PCR results in primate lung.
Figure 10:
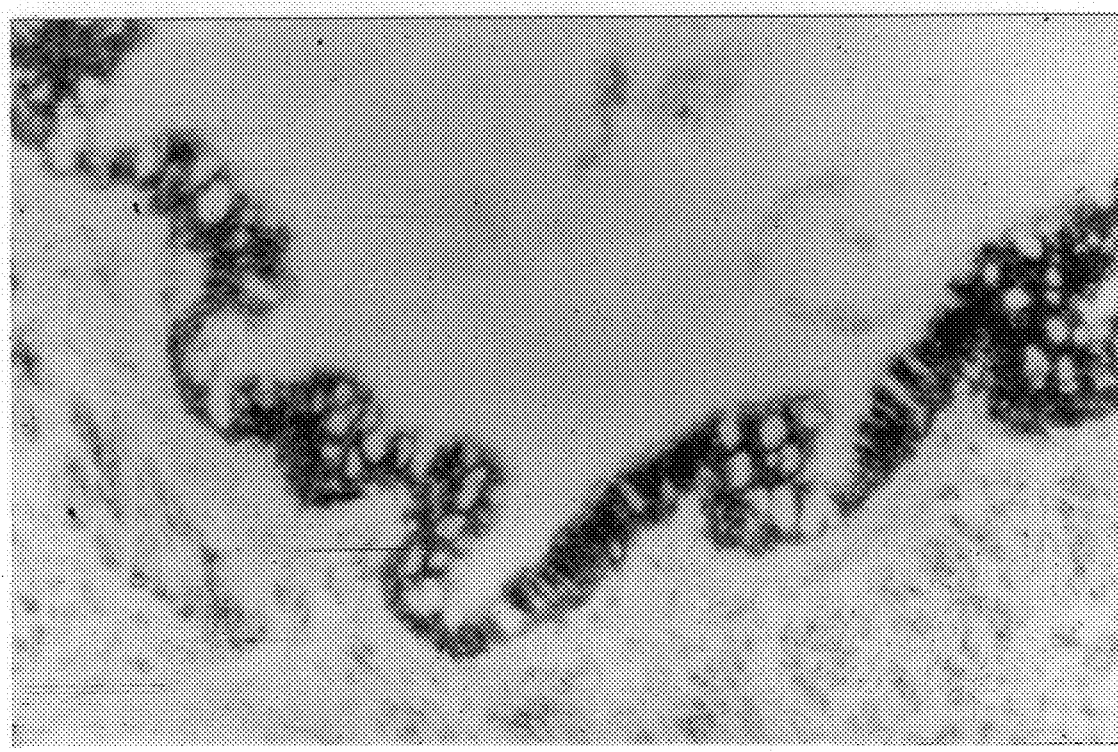
Figure 11:
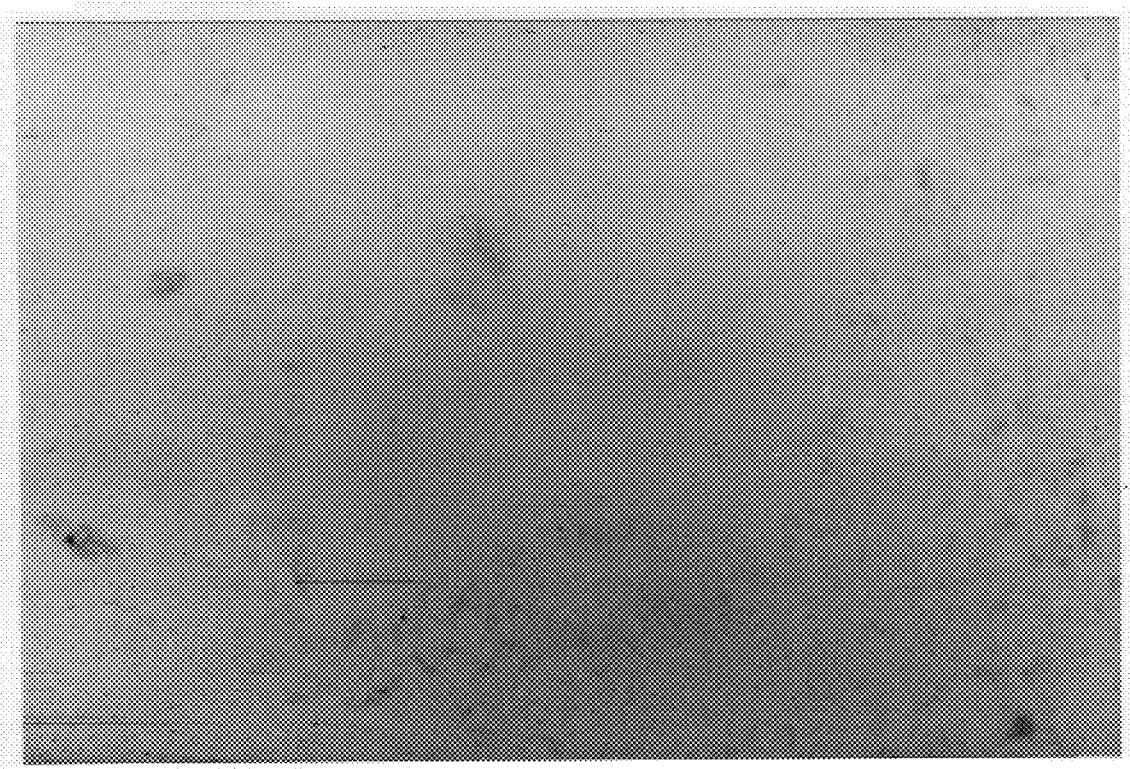
Figure 12:
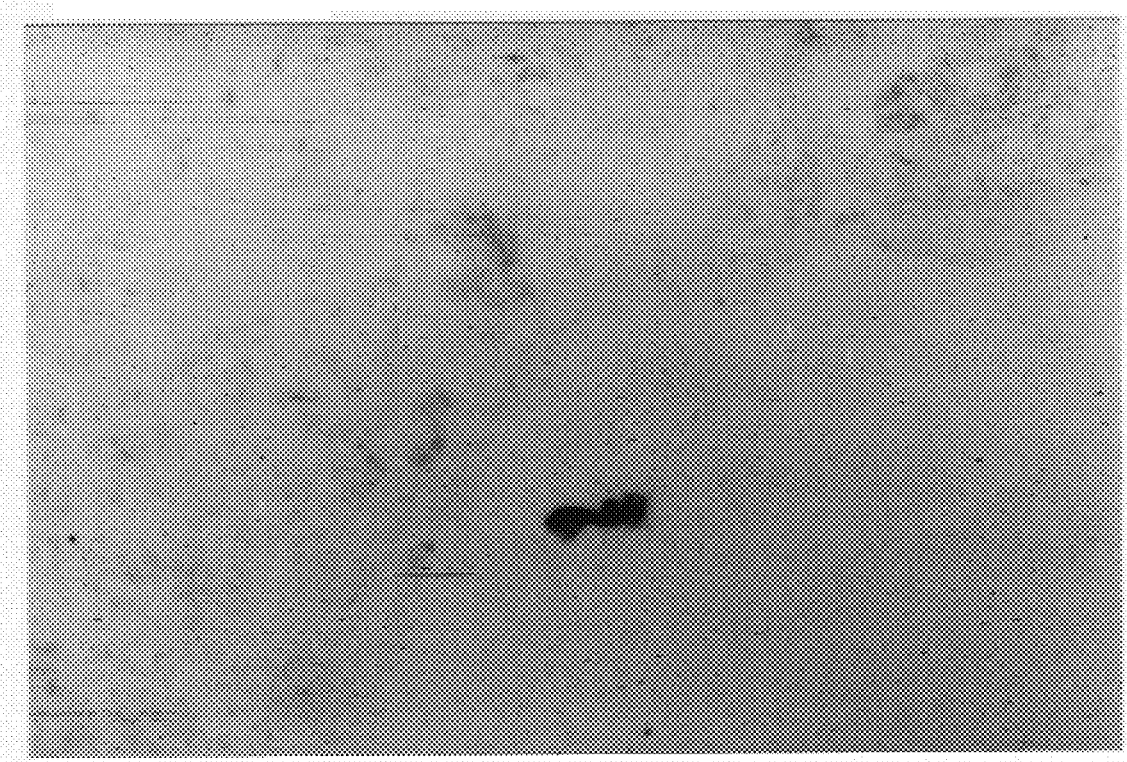
Figure 13:
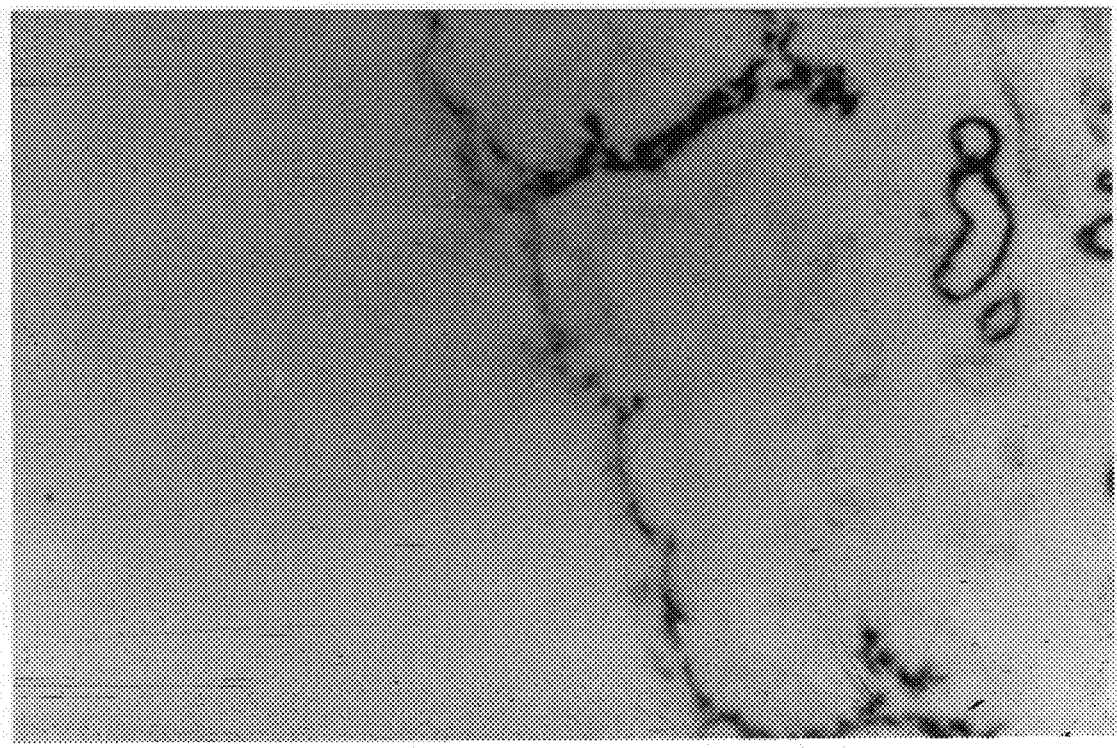
FIGS. 13–22 are photographs of immunohistochemistry of primate lung sections showing human CFTR expression analysis results.
Figure 14:
Figure 15:
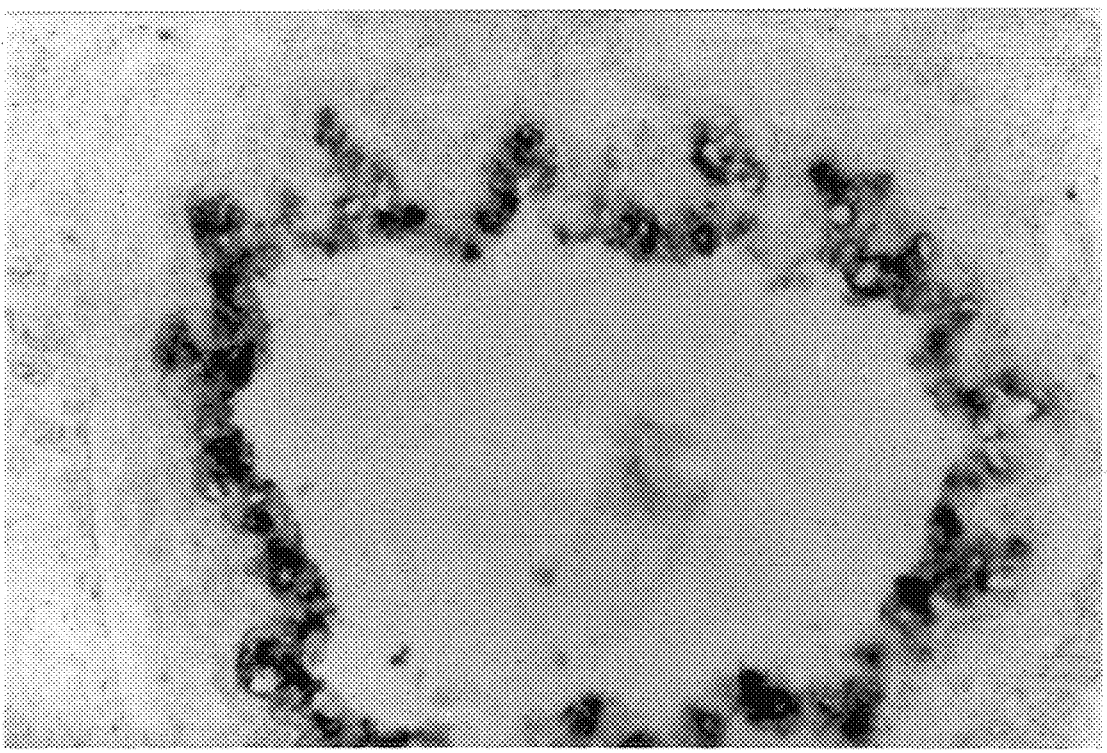
Figure 16:
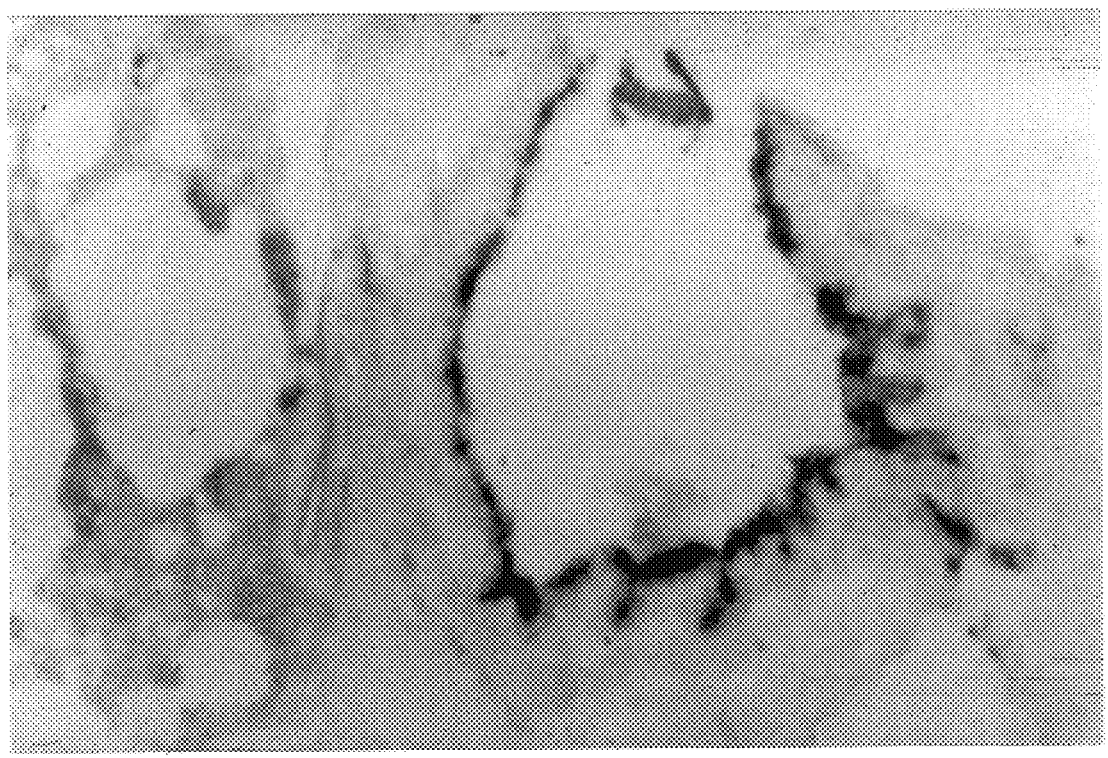

In tissues from untreated animals analyzed by in situ RT-PCR, no signal was detected, indicating that within the limits of sensitivity of this assay, endogenous CFTR was not detectable in untreated animals (FIG. 9). In contrast, a clear signal was observed in the cells lining the airway of the lungs in one of the treated animals (FIG. 10). This signal was found to be dependent on the presence of RNA (it was destroyed by RNase treatment) and the addition of reverse transcriptase (no signal was obtained in the absence of first-strand cDNA synthesis). Controls using DNase with no reverse transcriptase (FIG. 11) and DNase plus RNase treatment (FIG. 12) consistently showed no staining.

The RT-PCR data suggest that the vector specific primers can detect CFTR DNA and CFTR specific primers can detect DNA and RNA in both treated and untreated tissues. The signal obtained using CFTR specific primers in untreated tissue indicates that endogenous CFTR was being detected. Differences in sensitivity of these primers preclude their use as a direct measurement of transfection in whole tissue RT-PCR. However, since no signal was seen in untreated tissues with CFTR specific primers for in situ RT-PCR, it appears that these primers are useful for in situ RT-PCR.

Immunohistochemistry was also performed for detection of the CFTR protein with commercially available antibody (Genzyme) and proprietary antibodies. Genzyme antibodies were reactive to the R domain of CFTR and the carboxyl terminus of CFTR. A proprietary antibody (MB1) was produced in rabbits using the last 13 amino acids of the C-terminus of CFTR, as described by Marino et al. (1991, "Localization of the Cystic Fibrosis Transmembrane Conductance Regulator in Pancreas," *J. Clin. Invest.* 88,: 712–716). Tissues were collected in OCT and frozen in isopentane chilled in liquid nitrogen and stored at −70° C. until sectioning for immunohistochemistry. Standard immunohistochemistry procedures were used with alkaline phosphatase conjugated to goat anti-rabbit as the secondary antibody. Levamisole was used to inhibit endogenous alkaline phosphatase.

Figure 17:
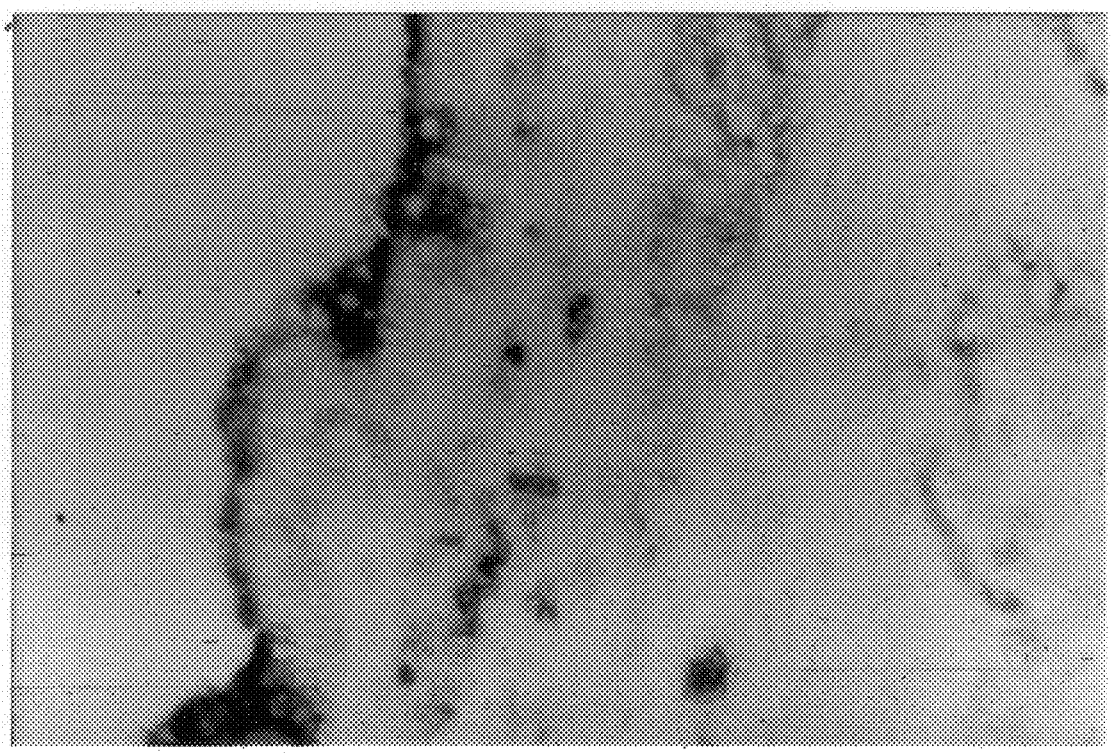
Figure 18:
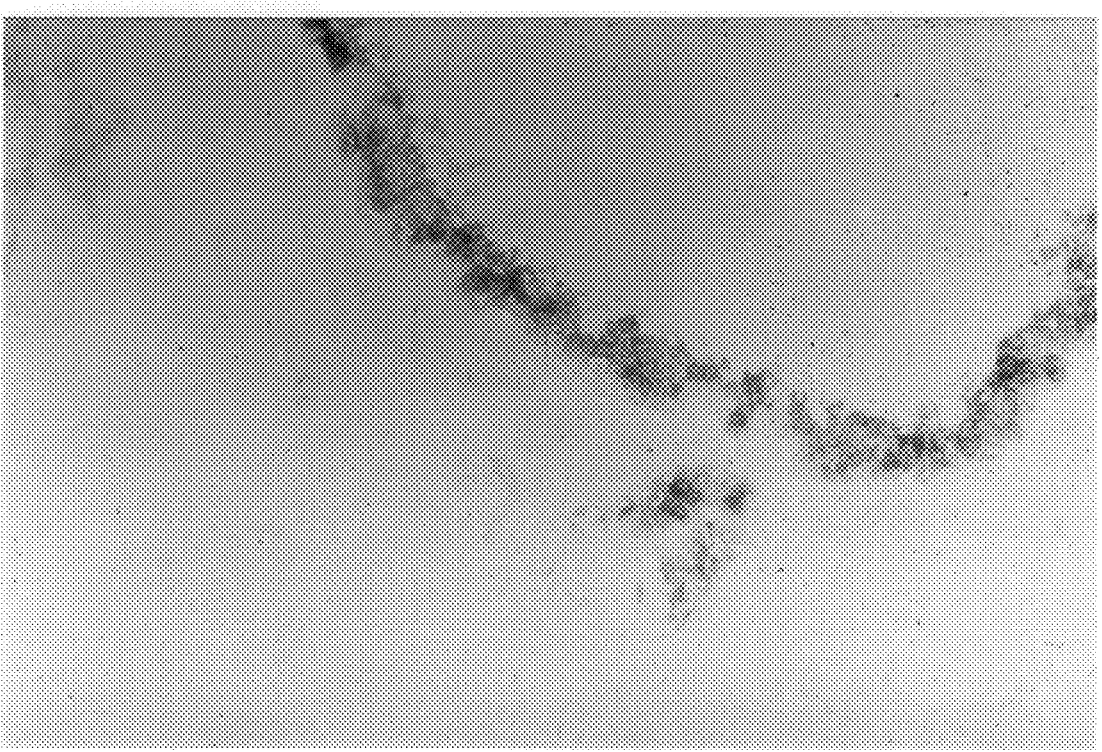
Figure 19:
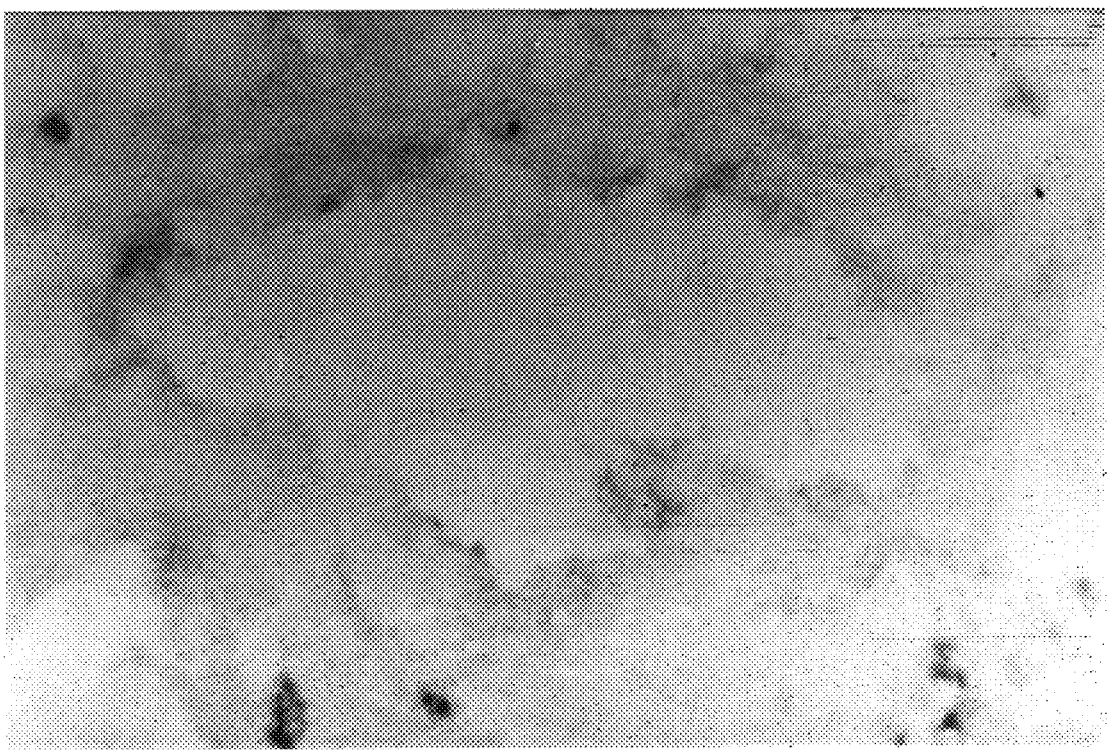
Figure 20:
Figure 21:
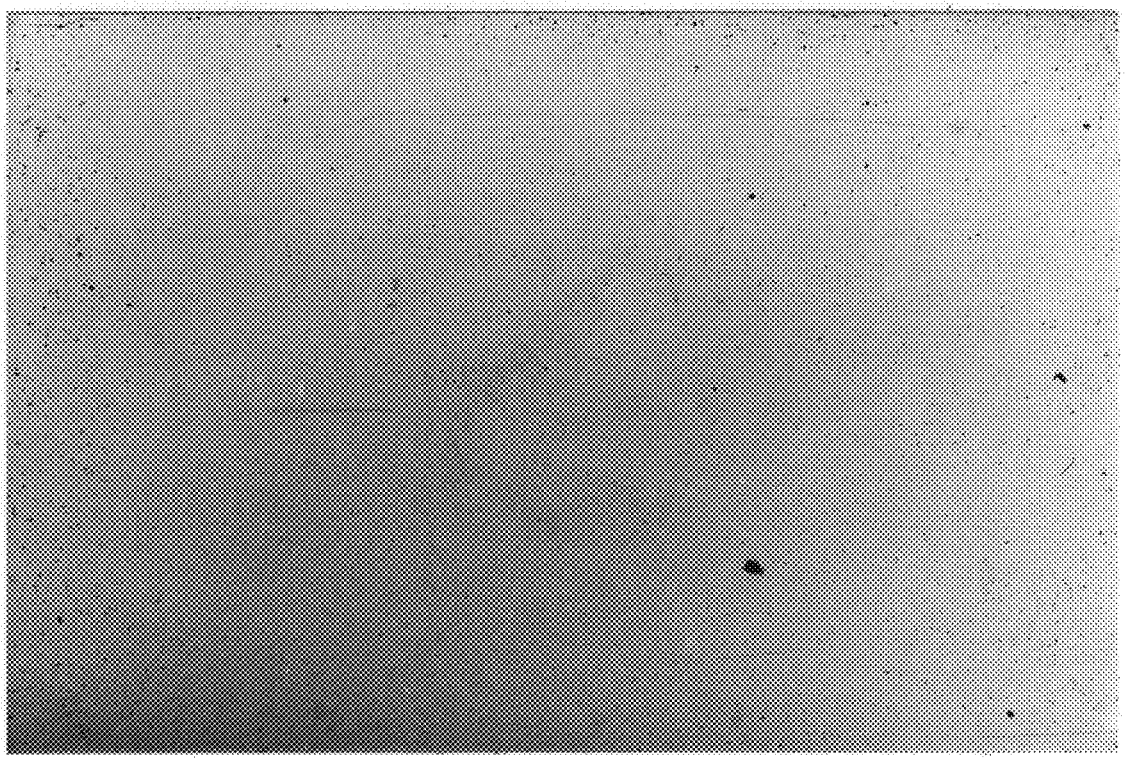
Figure 22:
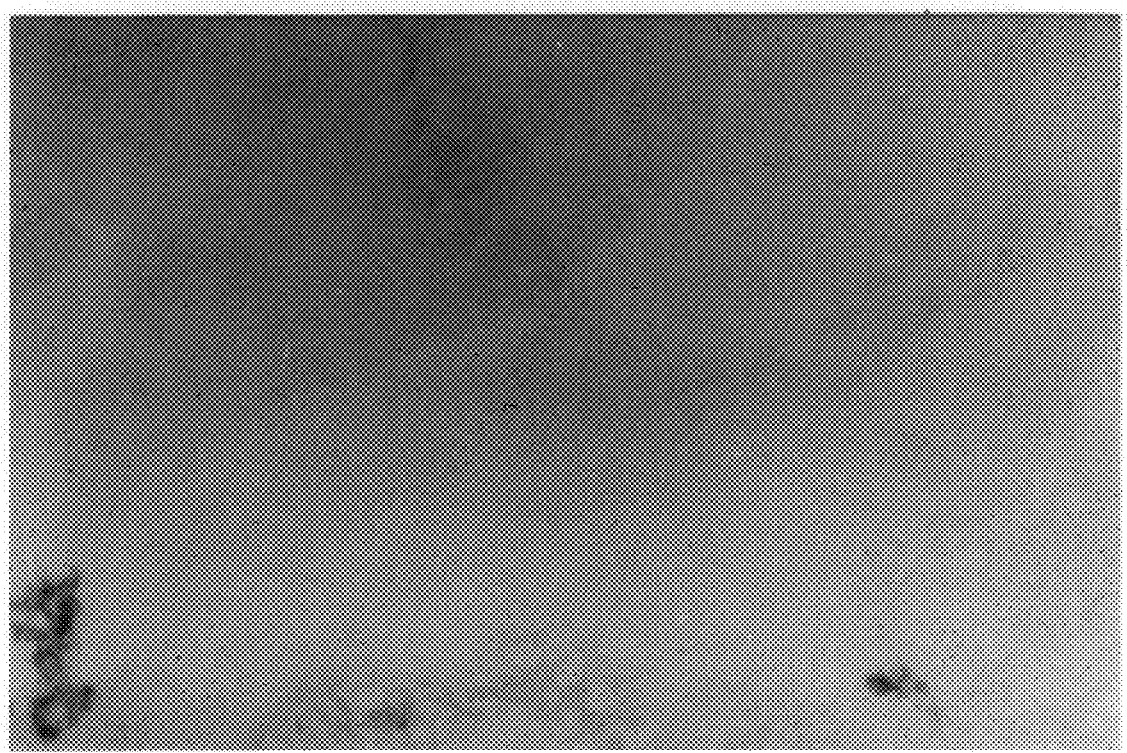

In sections of the trachea, right middle lobe, right anterior lobe and right caudal lobe, staining was apparent in the cells lining the airways in the treated animals. For the purposes of illustration, selected sections from Animal MMU25744 are shown: trachea, right anterior lung lobe, right middle lung lobe and right caudal lung lobe (corresponding to FIGS. 13–16). Comparable results were obtained in animal MMU25464 as demonstrated stained sections of trachea and right middle lung lobe (FIGS. 17–18). Untreated primates showed little to no staining in lung tissue (FIG. 19). Other controls included: an irrelevant first antibody (anti-CAT) (FIG. 20); incubation with second antibody without first antibody staining (FIG. 21); and he addition of excess free peptide to absorb CFTR-specific antibody prior to staining (FIG. 22). All controls were consistently negative.

Immunohistochemical analysis demonstrated transfection of the treated animals with staining apparent in the cells lining the airways. However, this assay is unable to assess the intracellular location of expressed CFTR protein. In samples from the treated animals, tracheal sections show 60–80% of the ciliated epithelial cells to be positive for CFTR protein with the apical regions of these cells staining most intensely. Immunostaining within the lung was confined principally to bronchi and bronchioles. Of these larger airways, 60–90% of the epithelial cells were positively stained. In some instances, staining within an individual airway was patchy with an abrupt transition between positively and negatively stained cells. Within the same section, a positively stained bronchiole and a closely adjacent negatively staining bronchiole could sometimes be seen. The high level of transfection appeared to diminish in the deeper regions of the lung, probably due to dosing limitations. At least 50% of the bronchi and bronchioles within a given section displayed significant staining. Alveolar macrophages in some sections also appeared to be staining; however, similar staining patterns can be seen in control sections. These results are substantially similar to the results obtained by in situ RT-PCR tissue section staining.

These results demonstrated functional delivery of a recombinant expression construct encoding human CFTR using the DNA:lipid complexes of the invention, and expression of human CFTR in primate lung tissues in vivo.

It should be understood that the foregoing disclosure emphasizes certain specific embodiments of the invention and that all modifications or alternatives equivalent thereto are within the spirit and scope of the invention as set forth in the appended claims.

We claim:

1. A composition comprising a formulation of a complex of a recombinant expression construct and a mixture of a neural lipid and a cationic lipid wherein
   (a) the recombinant expression construct comprises a nucleic acid encoding a protein and wherein said nucleic acid is operatively linked to gene expression regulatory elements; and
   (b) the cationic lipid is a compound having formula I:

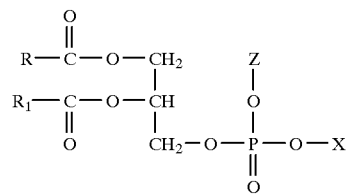

where Z is alkyl or alkylalkoxy, R and $R_1$ are independently straight-chain, aliphatic hydrocarbyl groups of from 11 to 29 carbon atoms and X is a cationic moiety of formula

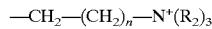

wherein n is an integer from 1 to 4 inclusive and each $R_2$ is independently hydrogen or lower alkyl and wherein the ratio of DNA to lipid ranges from about 1:1 to about 3:1 and wherein the nucleic acid comprising the recombinant expression construct is present in the complex at a concentration ranging of about 0.5 to about 5 mg/mL.

2. The composition of claim 1 wherein the cationic lipid is O-ethyl-dimyristoylphosphatidylcholine.

3. The composition of claim 1 wherein the neutral lipid is cholesterol or dioleoylphosphatidylethanolamine.

4. The composition of claim 1 wherein the cationic lipid is O-ethyl-dimyristoylphosphatidylcholine and the neutral lipid is cholesterol or dioleoylphosphatidylethanolamine.

5. The composition of claim 4 wherein the ratio of DNA to lipid ranges from about 1:1 to about 2:1.

6. The composition of claim 1 wherein the complex of a recombinant expression construct and a mixture of a neutral lipid and a cationic lipid comprises a ratio of DNA to lipid of 2:1.

7. The composition of claim 1 wherein the nucleic acid comprising the recombinant expression construct is present in the complex at a concentration of about 0.5 mg/mL to about 2 mg/mL.

8. The composition in claim 1 that encodes human CFTR.

9. A composition comprising a formulation of a complex of a recombinant expression construct and a mixture of a neutral lipid and O-ethyldimyristoylphosphatidylcholine as a cationic lipid, wherein the recombinant expression construct comprises a nucleic acid encoding a protein and wherein said nucleic acid is operatively linked to gene expression regulatory elements and wherein the ratio of DNA to lipid ranges from about 1:1 to about 3:1 and wherein the nucleic acid comprising the recombinant expression construct is present in the complex at a concentration ranging of about 0.5 to about 5 mg/mL.

10. The composition of claim 9 wherein the neutral lipid is cholesterol or dioleoylphosphatidylethanolamine.

11. The composition of claim 9 wherein the ratio of DNA to lipid ranges from about 1:1 to about 2:1.

12. The composition of claim 9 wherein the complex of a recombinant expression construct and a mixture of a neutral lipid and a cationic lipid comprises a ratio of DNA to lipid of 2:1.

13. The composition of claim 9 wherein the nucleic acid comprising the recombinant expression construct is present in the complex at a concentration of about 0.5 mg/mL to about 2 mg/mL.

14. The composition in claim 1 that encodes human CFTR.

* * * * *